(12) United States Patent
Barthel et al.

(10) Patent No.: US 7,528,102 B2
(45) Date of Patent: May 5, 2009

(54) FRAGRANCE RELEASE SYSTEM

(75) Inventors: Wolfgang Barthel, Langenfeld (DE);
Ion Canavoiu-Opritescu, Duesseldorf (DE); Matthias Reimann, Duesseldorf (DE); Arnd Kessler, Monheim (DE); Hans-Georg Muehlhausen, Duesseldorf (DE)

(73) Assignee: Henkel KGaA, Dusseldorf (DE)

( * ) Notice: Subject to any disclaimer, the term of this patent is extended or adjusted under 35 U.S.C. 154(b) by 723 days.

(21) Appl. No.: 11/054,264

(22) Filed: Feb. 9, 2005

(65) Prior Publication Data
US 2005/0148479 A1 Jul. 7, 2005

Related U.S. Application Data

(63) Continuation of application No. PCT/EP03/08853, filed on Aug. 8, 2003.

(30) Foreign Application Priority Data

Aug. 9, 2002 (DE) ................. 102 37 066
Jan. 29, 2003 (DE) ................. 103 03 352

(51) Int. Cl.
  *A61K 8/00* (2006.01)
  *C11D 3/50* (2006.01)
  *A61L 9/04* (2006.01)
  *A61L 9/00* (2006.01)
  *A61L 9/03* (2006.01)

(52) U.S. Cl. .................... 512/1; 510/101; 424/76.3; 424/76.4; 422/5

(58) Field of Classification Search .......... 512/1; 510/101; 424/76.3, 76.4; 422/5
See application file for complete search history.

(56) References Cited

U.S. PATENT DOCUMENTS

| 4,727,383 A | * | 2/1988 | Hill, III | 346/135.1 |
| 5,139,864 A | * | 8/1992 | Lindauer | 428/304.4 |
| 5,460,787 A | | 10/1995 | Colon | |
| 5,665,697 A | * | 9/1997 | Boden et al. | 512/13 |
| 5,861,128 A | * | 1/1999 | Vick et al. | 422/124 |
| 6,084,010 A | * | 7/2000 | Baetzold et al. | 523/210 |

(Continued)

FOREIGN PATENT DOCUMENTS

DE 100 36 850 A1 10/2001

(Continued)

OTHER PUBLICATIONS

Roempp Chemie Lexikon, Georg Thieme Verlag Stuttgart/New York, 9th Edition, p. 2507 (1990).

(Continued)

*Primary Examiner*—Mark Eashoo
*Assistant Examiner*—Michael Pepitone
(74) *Attorney, Agent, or Firm*—Paul & Paul

(57) ABSTRACT

A fragrance release system having a substantially rotationally symmetric container having a chamber accommodating a multitude of particles for deodorizing or fragrancing an open or closed space, the particles comprising a carrier material and at least one fragrance, and the container having a plurality of orifices through which emission of the fragrances of the particles from the accommodation chamber outward is possible, wherein the accommodation chamber (3) of the substantially rotationally symmetric container (2) has a crescent-like cross-sectional shape with a convex front wall (5) and a concave back wall (6).

38 Claims, 3 Drawing Sheets

U.S. PATENT DOCUMENTS

| | | | |
|---|---|---|---|
| 6,213,409 B1 * | 4/2001 | Warren et al. ............... | 239/53 |
| 6,235,705 B1 | 5/2001 | Zembrodt et al. | |
| 6,719,217 B1 * | 4/2004 | Tawara et al. ............ | 239/419.5 |
| 2002/0058595 A1 | 5/2002 | Kaiser | |
| 2003/0012680 A1 * | 1/2003 | Balsys ..................... | 422/5 |

FOREIGN PATENT DOCUMENTS

| | | |
|---|---|---|
| DE | 100 55 193 A1 | 1/2002 |
| DE | 102 37 066 A1 | 2/2004 |
| GB | 2324963 A * | 11/1998 |
| WO | WO 85/00981 A1 | 3/1985 |
| WO | WO 88/01503 A1 | 3/1988 |
| WO | WO 91/00744 A1 | 1/1991 |
| WO | WO 02/00979 A1 | 2/2002 |
| WO | WO 03/042462 A2 | 5/2003 |

OTHER PUBLICATIONS

Roempp Chemie Lexikon, Georg Thieme Verlag Stuttgart/New York, 9th Edition, p. 3168 (1991).

* cited by examiner

FRAGRANCE RELEASE SYSTEM

CROSS REFERENCE TO RELATED APPLICATIONS

This application is a continuation under 35 U.S.C. § 365(c) and 35 U.S.C. § 120 of international application PCT/EP2003/008853, filed Aug. 8, 2003, incorporated by reference herein in its entirety. This application also claims priority under 35 U.S.C. § 119 of DE 102 37 066.4, filed Aug. 9, 2002 and DE 103 03 352.1, filed Jan. 29, 2003, each of which is incorporated by reference herein in its entirety.

BACKGROUND OF THE INVENTION

The invention relates to a fragrance release system comprising a container and a multitude of particles accommodated in the accommodation chamber of the container for deodorizing and/or fragrancing open or closed spaces, especially machine dishwasher or textile washing machines or laundry dryers, said particles having a preferably polymeric carrier material and at least one fragrance, and said container having a plurality of orifices through which emission of the fragrances of the particles from the accommodation chamber outward is possible.

In closed spaces without sufficient fresh air supply, unpleasant odors frequently occur. Such spaces may, for example, be the interiors of machine dishwashers when the dishes present there are very highly soiled and/or remain in the dishwasher over a prolonged period before the washing operation. In order to remove or to reduce such odors, machine dishwasher deodorants are known for machine dishwashers. These deodorants may be formulated in very different ways. For the consumer, it is desirable to obtain an article for deodorizing machine dishwashers or other closed spaces which has an intense product fragrance when it is produced, which not only ensures product identification, but simultaneously conveys the impression of high efficacy and ensures a very reliable release of constant amounts of fragrance in the course of its lifetime. A series of different deodorants for machine dishwashers is described in the prior art.

A fragrance release system as per the preamble of claim 1 is known from WO 02/09779 A1. This known fragrance release system has a container in which a multitude of small particles laden with fragrances is accommodated. The container is provided with a multitude of orifices whose size is dimensioned such that the small particles cannot escape through the orifices. On the other hand, the orifices are dimensioned such that emission of the fragrances of the particles from the accommodation chamber of the container outward is possible. The container itself preferably has an approximately cuboidal shape, with rounded corners and an openable and closable lid. The accommodation chamber of the container may be divided into two sections in which perfumed particles are disposed. The particles themselves consist preferably of a polymeric carrier material which is laden with a fragrance.

In the known fragrance release system, the container is filled with particles preferably between 5 and 95% of the volume of the accommodation chamber, because a maximum particle volume but equally free mobility of the particles should be achieved.

However, the known fragrance release system is afflicted with disadvantages, some of which can be attributed to the design of the container, since the container shape described is suited very little, for example, to accommodation in a machine dishwasher or the like, since the container is relatively large. Another disadvantage is that it is virtually impossible in the case of the selected container shape to virtually fully fill the accommodation chamber of the container with particles, which is desirable because mobility of the particles is undesired especially in the case of use within a machine dishwasher, since virtually the entire surface area of all particles is simultaneously available for fragrance release and the functioning time of the system is limited.

Other solutions for the deodorization and/or fragrancing of washing basins or else machine dishwashers are known from DE 100 55 193 A1 and DE 100 36 850 A1.

Fragrance-containing articles made of ethylene/vinyl acetate copolymer are disclosed in the publication WO 91/00744 A1. These are injection-molded plastics plaques which can be hung in the machine dishwasher. Since the fragrance is mixed with the plastic before the injection molding, it is exposed to high thermal stress during the processing. Such thermal stress leads to a partial loss of fragrances as a result of evaporation or thermal decomposition. Such plastics plaques likewise do not exhibit a constant release profile for the fragrances present over their use time.

The publication WO 85/00981 A1 provides a process for impregnating plastics particles with fragrances at low temperatures. One possible use of the particles is for deodorization in machine dishwashers. These particles are said to be effective for between ten and twenty wash cycles.

The prior art also discloses deodorants for use in laundry dryers; for instance, the publication U.S. Pat. No. 6,235,705 B1 describes a product for fragrancing in laundry dryers which consists of fragrance-containing plastics pearls in a mesh bag. The pearls are fragranced during their production at elevated temperature.

It is an object of the invention to improve a fragrance release system as per the preamble of claim 1 such that effective fragrance release is ensured even over a prolonged period with minimum space requirement of the container.

It is a further object of the invention to provide a composition for deodorizing spaces, especially machine dishwasher interiors, which has an increased fragrance release at the start of use (product identification, demonstration of efficacy) and subsequently reduced but constant fragrancing, the composition being active over a long period and its efficacy being independent of environmental factors such as temperature, moisture or alkalinity.

According to the invention, the object is achieved by the features of claim 1. The subclaims 2 to 20 which follow describe further embodiments.

DESCRIPTION OF THE INVENTION

The inventive fragrance release system has an accommodation chamber of a substantially rotationally symmetric container which has a crescent-like cross-sectional shape with a convex front wall and a concave back wall. It thus comprises a container which has a shape which corresponds approximately to the shape of a toadstool head, and the rotationally symmetric accommodation chamber has an approximately crescent-like cross section.

It has been found that this container shape has an optimum ratio between the total surface area of all particles in the starting state to the total surface area of the accommodation chamber, i.e. the outer surface of the particles after the first use when the melting or softening point of the particles has been exceeded. This ratio is substantially more favorable than in known container shapes, and is also distinctly more favorable than other container shapes (for example sphere). The surface area of the particle conglomerate is sufficiently large to ensure effective fragrance release. The particles consist preferably of those materials as described in particular in the claims of the aforementioned patent application, which are explicitly incorporated by reference as a constituent of the disclosure content of this application.

Preference is given to providing that the accommodation chamber is filled fully with particles.

As a result of the configuration of the fragrance release system, the particles are not arranged loosely in the container and, after the first use after appropriate heating, form a cross-sectionally crescent-shaped conglomerate, which results in the surface area of the polymer particles being reduced and longer functionality of the system being enabled. If, in contrast, the particles were to be freely mobile within the container, the functioning time of the system would be dependent only on the amount of fragrance which is present in each particle; the number of particles would only influence the fragrance intesity. The reduction in the surface area of the particles achieves the effect that they cannot release their fragrance all at once; the fragrance intensity is determined by the amount of particles at the surface of the conglomerate, i.e. at the inner walls of the container in direct contact with the air. Fragrances from the inner particles migrate progressively to the surface of the conglomerate; the inner particles thus have a depot function for the fragrance release system and enable a substantially longer functioning time compared to known systems.

A preferred embodiment provides that the two end regions of the crescent-like cross-sectional shape of the accommodation chamber are rounded. The corresponding outer edge region of the container is thus rounded or bulge-like, so that this region too can be filled fully with particles, which allows the space requirement of the container to be kept small, which is significant, for example, in the case of use in a machine dishwasher.

The container may in principle be produced in different ways; for example, it may be produced in one piece by a blow-molding operation and then filled with the particles through an orifice in the container, in which case this orifice is subsequently closed after the filling.

However, very particular preference is given to providing that the container is designed in two parts, one part having the back wall and the other part the front wall. The two parts of the container may then be produced in a simple manner in an injection molding process.

In order to be able to connect the two container parts together in a very simple manner, preference is given to providing that the part of the container having the back wall has a bulge-like edge region which is connected to a strut-like edge region of the other part.

The two parts may be connected to one another in different ways; they are preferably connected to one another by means of a snap-in connection.

In order to ensure substantially full filling of the container with particles in a simple manner in the case of the two-part design of the container, very particular preference is given to providing that the concave back wall curves inward in a conelike manner in its middle region. In the filling position, the other part having the convex front wall then initially forms the receptacle for the particles. The amount of particles required to fully fill the container is introduced into this container part, so that the fill level remains somewhat below the edge of the container part. Subsequently, the part having the concave back wall is placed on effectively as a lid and snapped in. The middle, cone-shaped concave region displaces the particles outward and upward, and they also get into the regions of the thus formed accommodation chamber which have not yet been filled. The dimensioning is such that, before the particles reach the edge, the bulge-like edge region of one part reaches the strut-like edge region of the other part, so that the particles cannot fall out.

A very particularly preferred configuration provides that the container of the fragrance release system or its accommodation chamber is dimensioned such that the ratio of the total surface area of all particles in the starting state (i.e. before they are heated or softened for the first time) to the total surface area of the accommodation chamber is between 1:0.35 and 1:0.36. Such an optimal ratio can be achieved by the selected container shape. Accordingly, for example in the case of a spherical container, only a ratio of 1:0.227 is achievable which, as has been shown, is insufficient to ensure effective fragrance release with comparable total volume of the particles.

In addition, the container is preferably configured such that the layer thickness of the particles in the accommodation chamber filled virtually fully with particles is between 10 and 12 mm and the volume of the accommodation chamber is preferably from 10 to 500 ml, preferably about 40 ml. The volume is dependent upon the intended use of the fragrance release system.

In order to be able to mount the fragrance release system in a simple manner, for example in a machine dishwasher, the container has on its exterior a hanging device with which the fragrance release system can be hung preferably in the upper carriage of a machine dishwasher. Alternatives are securing means such as adhesive surfaces, with which the device can be fixed to walls of chambers.

In addition to the orifices for emitting the fragrances, the container preferably has a multitude of slot-shaped orifices in the region of the back wall, through which, for example, a certain amount of moisture can get into the container interior and out of it during the wash cycle within a machine dishwasher, which can lead to improved fragrance release.

In the context of the present application, the term "polymers" embraces addition polymers, polyadducts and polycondensates.

In this application, addition polymers refer to those high molecular weight compounds which are formed by a chain growth mechanism. Preferred addition polymers in the context of the present application are polyethylene, polypropylene, poly-1-butene, poly-4-methyl-1-pentene, polyvinyl chloride, polyvinylidene chloride, polyacrylonitrile and/or polystyrene.

Polyadducts are formed by polyaddition, i.e. poly reactions, in which repeating and mutually independent linkage reactions of bis- or polyfunctional reactants (monomers) result via reactive oligomers finally in polymers. Preferred polyadducts are polyurethanes.

Like the polyadducts, polycondensates are formed as a result of repeating and mutually independent linkage reactions of discrete oligomers and monomers, except that, in contrast to polyaddition, there is simultaneous elimination of low molecular weight compounds. Preferred polycondensates in the context of the present invention are polyamides, polycarbonates and polyesters.

In summary, the containers for accommodating the fragrance-containing particles comprise at least a proportion of polyethylene, polypropylene, polyethylene/polypropylene copolymers, polyether/polyamide block copolymers, styrene/butadiene (block) copolymers, styrene/isoprene (block) copolymers, styrene/ethylene/butylene copolymers, acrylonitrile/butadiene/styrene copolymers, acrylonitrile/butadiene copolymers, polyether esters, polyisobutene, polyisoprene, ethylene/ethyl acrylate copolymers, polyamides, polycarbonate, polyester, polyacrylonitrile, polymethyl methacrylate or polyurethanes.

Polymers are notable for particular versatility also with regard to their processibility. It is equally possible to process plastics with shaping by extrusion or injection-molding processes as it is by thermoforming processes. In the course of thermoforming (warm shaping), a preheated plastics plaque or film is introduced between the two parts of the tool, the positive and the negative, which are then compressed together, which results in the plastics part obtaining its shape. What is known as cold shaping proceeds similarly; here, however, the plaque or film to be shaped is not preheated. When there is no negative tool, this is referred to as deep drawing. In the context of the present invention, the abovementioned containers may be produced by all processes known to those skilled in the art, in particular by extrusion, injection molding, thermoforming or blow molding. In any case, the containers have to enable the escape of fragrance and optional other active ingredients, for which purpose both the use of containers equipped with orifices and the at least proportional use of permeable container materials as permeable membranes is suitable.

In the context of the present application, "textile material" refers to those substances which can be processed to textile fabrics. In addition to the synthetic polymers such as nylon, polyester, polyacrylic or polyolefins, the preferred textile materials also include the vegetable materials such as cotton or other cellulosic materials.

Depending upon the type of production process selected and/or a selected coating, the surface of the solid particles may have unevenness.

Further suitable container shapes are bags, nets, sacks, pouches or sachets, which can be produced, for example, from films, nonwovens, wovens or loop-drawn knits, and their pore or mesh width, as in the case of the aforementioned injection moldings, blow moldings or thermoformings, has to be lower than the diameter of the particles in order to prevent trickling out.

After the introduction of the fragrance-containing particles, the aforementioned containers have to be sealed by sewing, fusion bonding or adhesion bonding.

Preference is given to providing that the accommodation chamber is filled fully with particles.

The subject matter of the invention is in principle not restricted to use in closed spaces, but rather is suitable as a frangrance release system for deodorizing and fragrancing ambient air, for example of restrooms, for which the fragrance release system is mounted in the region of the toilet bowl or its environment. The publication WO 03/042462 A2, for example, describes a device for the toilet bowl with two different chambers, of which one chamber contains a detergent and one chamber a fragrance. However, the chamber for the detergent has to be placed within the flush stream of the water and the chamber for the fragrance outside it. An inventive design of the fragrance chamber of devices for the toilet bowl makes the position of the fragrance chamber independent, i.e. it may be disposed outside or else within the flush stream.

It has been found that the further object is achieved by fragrance release systems which have certain polymeric carrier materials. The present application therefore also provides a fragrance release system comprising a vessel and particles for deodorizing and fragrancing spaces, which comprises at least one polymeric carrier material having a melting or softening point between 30 and 150° C. and at least one fragrance. In the case of this fragrance release system, particles are used whose polymeric carrier material has a softening or melting point between 30° and 150° C. and even more preferably between 75° and 80° C. Such a fragrance release system has an optimized fragrance release profile which is based on a change in the ratios of surface area to internal volume of the particles present in the fragrance release system. In a brand new, unused system, these particles are present as singular individual particles having a large particle surface area. However, the composition of the particles is selected such that, in the event of thermal stress on these particles, the surface of the polymeric carrier material of these particles softens or melts and individual particles adhere together with reduction of the overall surface area. The magnitude of the melting or softening point of the polymeric carrier materials is determined by the field of use. For example, maximum temperatures between 65° and 75° C. occur during machine dishwashing, especially in the rinse cycle. The container of this fragrance release system consists preferably of a water-insoluble organic or inorganic material, such as plastic, ceramic, glass, metal or textiles.

Such materials are noticeable for particular versatility, also with regard to their processability. For instance, it is equally possible to process them with shaping by extrusion or injection molding processes as it is by thermoforming processes. In particular, production by extrusion, injection molding, thermoforming or blow molding is possible. The geometric shapes provided for the container may be cylinders, spheres, hemispheres or "stretched spheres" in the form of ellipsoidal capsules, or may be regular polyhedra, for example tetrahedra, hexahedra, octahedra, dodecahedra, icosahedra. After the filling with the particles, these containers are closed to form the fragrance release system in order to preclude trickling-out of the particles. However, a disadvantage in the case of this fragrance release system is the container shapes selected hitherto, since it has not been possible in the case of these containers to achieve an optimal ratio between the total volume of the particles and the surface area of the particle conglomerate.

The improved fragrance release of inventive fragrance release systems is based on a change in the ratio of surface area to internal volume of the particles present in the fragrance release system. In a brand new, unused system, these particles are present as singular particles with large particle surface area. However, the composition of the particles is selected such that, in the event of thermal stress on these particles, the surface of the polymeric support material of these particles is softened or melted and individual particles adhere together with reduction of the overall surface area. The magnitude of the melting or softening point of the polymeric support materials is accordingly determined by the field of use of inventive compositions. For example, maximum temperatures between 65 and 75° C. occur during machine dishwashing, especially in the rinse cycle. When inventive compositions serve to fragrance spaces in buildings or vehicles, for example as an attachment for heaters, the maximum temperatures attained there are generally in the range from 70 to 90° C. In any case, the melting or softening points of the particles should be above the ambient temperature customary in the course of the transport and storage thereof and below the decomposition temperatures of the fragrances present.

Suitable polymeric carrier materials for the fragrance-containing particles are generally all polymers or polymer mixtures which satisfy the abovementioned criteria with regard to the melting or softening temperature. Fragrance release systems preferred in the context of the present application are characterized in that the polymeric carrier material comprises at least one substance from the group consisting of ethylene/vinyl acetate copolymers, low- or high-density polyethylene (LDPE, HDPE) or mixtures thereof, polypropylene, polyethylene/polypropylene copolymers, polyether/polyamide block copolymers, styrene/butadiene (block) copolymers, styrene/isoprene (block) copolymers, styrene/ethylene/butylene copolymers, acrylonitrile/butadiene/styrene copolymers, acrylonitrile/butadiene copolymers, polyether esters, polyisobutene, polyisoprene, ethylene/ethyl acrylate copolymers, polyamides, polycarbonate, polyester, polyacrylonitrile, polymethyl methacrylate, polyurethanes, polyvinyl alcohols.

Polyethylene (PE) is a collective term for the polymers which belong to the polyolefins and have moieties of the $CH_2$—$CH_2$ type as a characteristic base unit of the polymer chain. Polyethylenes are prepared generally by addition polymerization of ethylene by two fundamentally different methods, the high-pressure and the low-pressure process. The resulting products are correspondingly frequently referred to as high-pressure polyethylenes and low-pressure polyethylenes respectively; they differ mainly with regard to their degree of branching and, associated with this, in their degree of crystallinity and their density. Both processes may be carried out as a solution polymerization, emulsion polymerization or gas phase polymerization.

In the high-pressure process, branched polyethylenes of low density (approx. 0.915-0.935 g/cm$^3$), and degrees of crystallinity of approx. 40-50% are achieved, which are referred to as LDPE (low-density polyethylene) types. Products of higher molar mass and, as a result of this, improved strength and stretchability have the abbreviation HMW-LDPE (HMW=high molecular weight). Copolymerization of ethylene with longer-chain olefins, especially with butene and octene, allows the marked degree of branching of the polyethylenes prepared in the high-pressure process to be reduced; the copolymers have the abbreviation LLD-PE (linear low-density polyethylene).

The macromolecules of the polyethylenes from low-pressure processes are substantially linear and unbranched. These polyethylenes, abbreviated to HDPE (high-density polyethylene), have degrees of crystallinity of 60-80% and a density of approx. 0.94-0.965 g/cm$^3$. They are supplied as products having high and ultrahigh molar mass (approx. 200 000-5 000 000 g/mol and 3 000 000-6 000 000 g/mol respectively), under the abbreviation HD-HMW-PE and UHMW-HD-PE respectively. Products of medium density (MDPE) composed of mixtures of polyethylenes of low and high density are also commercially available. Linear polyethylenes having densities of <0.918 g/cm$^3$ (VLD-PE, very low-density polyethylene) are only slowly gaining importance on the market.

Polyethylenes have a very low water vapor permeability; the diffusion of gases, and also of aromas and ethereal substances, through polyethylene is relatively high. The mechanical properties are greatly dependent upon molecular size and structure of the polyethylenes. Generally, degree of crystallinity and density of polyethylenes increase with decreasing degree of branching and with shortening of the side chains. Shear modulus, hardness, stretching limit and melting range increase with density; shock resistance, transparency, swellability and solubility decrease. At the same density, tensile strain at break, elongation, shock resistance, impact strength and sustained use strength increase with rising molar mass of the polyethylenes. Depending on the procedure in the polymerization, it is possible to obtain products having paraffin wax-like properties (MR about 2000) and products of maximum toughness (MR above 1 million).

The polyethylene types may be processed by all methods customary for thermoplastics.

Polypropylene (PP) is the name for thermoplastic polymers of propylene with the general formula:

The basis of polypropylene preparation was the development of the process for the stereospecific polymerization of propylene in the gas phase or in suspension by Natta. This is initiated by Ziegler-Natta catalysts, but to an increasing degree also by metallocene catalysts, and leads either to highly crystalline isotactic or to less crystalline syndiotactic or to amorphous atactic polypropylenes.

Polypropylene features high hardness, rebound resilience, stiffness and heat resistance. It is possible to briefly heat objects made of propylene even up to 140° C. At temperatures below 0° C., a certain embrittlement of the polypropylenes occurs, but can be shifted to substantially lower temperature ranges by copolymerization of the propylene with ethylene (EPM, EPDM). Generally, the impact strength of polypropylene can be improved by modification with elastomers. As in the case of all polyolefins, the chemical resistance is good. An improvement in the mechanical properties of the polypropylenes is achieved by reinforcing with talc, chalk, wood meal or glass fibers. Polypropylenes are oxidation- and light-sensitive to an even greater degree than PE, which is why it is necessary to add stabilizers (antioxidants, light stabilizers, UV absorbers).

Polyethers is an umbrella term in the field of macromolecular chemistry for polymers whose organic repeating units are held together by ether functionalities (C—O—C). According to this definition, a multitude of structurally very different polymers belongs to the polyethers, for example the polyalkylene glycols (polyethylene glycols, polypropylene glycols and polyepichlorohydrins) as polymers of 1,2-epoxides, epoxy resins, polytetrahydrofurans (polytetramethylene glycols), polyoxetanes, polyphenylene ethers (see polyaryl ethers) or polyether ether ketones (see polyether ketones). The polyethers do not include polymers having pendent ether groups, including the cellulose ethers, starch ethers and vinyl ether polymers.

The group of the polyethers also includes functionalized polyethers, i.e. compounds having a polyether structure which also bear, attached pendent to their main chains, other functional groups, for example carboxyl, epoxy, allyl or amino groups, etc. Block copolymers of polyethers and polyamides (known as polyether amides or polyether block amides, PEBA) have a variety of possible uses.

Polyamides (PA) refer to polymers whose basic units are held together by amide bonds (—NH—CO—) Naturally occurring polyamides are peptides, polypeptides and proteins (for example albumin, wool, silk). Apart from a few exceptions, the synthetic polyamides are thermoplastic, catenated polymers, some of which have gained great industrial significance as synthetic fibers and materials. According to the chemical structure, what are known as the homopolyamides can be divided into two groups, the aminocarboxylic acid types (AC) and the diamine-dicarboxylic acid types (AA-CC; A denotes amino groups and C carboxyl groups). The former are prepared from only a single monomer by, for example, polycondensation of an ω-aminocarboxylic acid (1) (polyamino acids) or by ring-opening polymerization of cyclic amides (lactams) (2).

In addition to the homopolyamides, some copolyamides have also gained significance. It is customary to qualitatively and quantitatively specify the composition, for example PA 66/6 (80:20) for polyamides prepared from 1,6-hexanediamine, adipic acid and ε-caprolactam in a molar ratio of 80:80:20.

Owing to their special properties, polyamides which contain exclusively aromatic radicals (for example those made from p-phenylenediamine and terephthalic acid) are embraced under the generic name of aramids or polyaramids (for example Nomex®).

The most frequently used polyamide types (in particular PA 6 and PA 66) consist of unbranched chains with average molar masses of from 15 000 to 50 000 g/mol. They are semicrystalline in the solid state and have degress of crystallization of 30-60%. An exception is that of polyamides made from units having side chains or copolyamides made from highly differing components, which are substantially amorphous. In contrast to the generally milky, opaque semicrystalline polyamides, these are almost glass-clear. The softening temperature of the most commonly used homopolyamides is between 200 and 260° C. (PA 6: 215-220° C., PA 66: 255-260° C.).

Polyesters is the collective term for polymers whose basic units are held together by ester bonds (—CO—O—). According to their chemical structure, what are known as the homopolyesters can be divided into two groups, the hydroxycarboxylic acid types (AB polyesters) and the dihydroxydicarboxylic acid types (AA-BB polyesters). The former are prepared from only a single monomer by, for example, polycondensation of an ω-hydroxycarboxylic acid 1 or by ring-opening polymerization of cyclic esters (lactones) 2.

Branched and crosslinked polyesters are obtained in the polycondensation of tri- or polyhydric alcohols with polyfunctional carboxylic acids. The polyesters generally also include the polycarbonates (polyesters of carbonic acid).

AB-type polyesters (I) include polyglycolic acids, polylactic acids, polyhydroxybutyric acid [poly(3-hydroxybutyric acid)], poly(ε-caprolactone)s and polyhydroxybenzoic acids.

Purely aliphatic AA-BB-type polyesters (II) are polycondensates of aliphatic diols and dicarboxylic acids which can be used, among other uses, as products having terminal hydroxyl groups (as polydiols) for the preparation of polyester polyurethanes [for example polytetramethylene adipate]. In quantitative terms, the greatest industrial significance is possessed by AA-BB-type polyesters made from aliphatic diols and aromatic dicarboxylic acids, in particular the polyalkylene terephthalates, with polyethylene terephthalate (PET), polybutylene terephthalate (PBT) and poly(1,4-cyclohexane-dimethylene terephthalate)s (PCDT) as the most important representatives. The properties of these types of polyesters can be varied widely by also using other aromatic dicarboxylic acids (e.g. isophthalic acid) or by using diol mixtures in the polycondensation, and they can be adapted to different fields of use.

Purely aromatic polyesters are the polyarylates, which include poly(4-hydroxybenzoic acid). In addition to the saturated polyesters mentioned hitherto, it is also possible to prepare unsaturated polyesters from unsaturated dicarboxylic acids, which have gained industrial significance as polyester resins, in particular as unsaturated polyester resins (UP resins).

Polyesters are generally thermoplastics. Products based on aromatic dicarboxylic acids have marked materials character. The purely aromatic polyarylates feature high thermal stability.

Polyurethanes (PUR) denote polymers in whose macromolecules the repeating units are joined by urethane moieties —NH—CO—O—. Polyurethanes are obtained generally by polyaddition of dihydric or higher polyhydric alcohols and isocyanates.

Depending on the selection and stoichiometric ratio of the starting materials, polyurethanes are thus formed which have very different mechanical properties and can be used as constituents of adhesives and coatings (polyurethane resins), as ionomers, as a thermoplastic material for bearing parts, castors, tires, rolls, and as more or less hard elastomers in fiber form (elastomeric fibers, abbreviated to PUE for these elastan or spandex fibers) or as polyether or polyesterurethane rubber (EU and AU respectively).

Polyurethane foams are formed in the polyaddition when water and/or carboxylic acids are present because these react with the isocyanates with the elimination of carbon dioxide which has a swelling and foam-forming action. The use of polyalkylene glycol ethers as diols and water as a reaction component leads to flexible polyurethane foams; the use of polyols and propellant gases from CFCs (particularly R11) affords rigid polyurethane foams and structural or integral foams. Examples of assistants additionally required here are catalysts, emulsifiers, foam stabilizers (particularly polysiloxane-polyether copolymers), pigments, aging inhibitors and flame retardants. For the production of objects made of polyurethane foam, even those having a complicated shape, what is known as the RIM technique (reaction injection molding) was developed in the 1970s. The RIM process is based on rapid metering and mixing of the components, injection of the reactive mixture into the mold and rapid curing; the cycle time is only a few minutes. By means of the RIM technique, objects including automotive bodywork parts, shoe soles, window profiles and television casings are obtained.

Polyvinyl alcohols (PVAL, occasionally also PVOH) is the term for polymers of the general structure

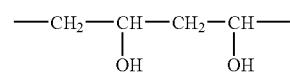

which also contain structural units of the

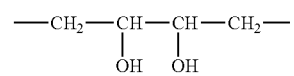

type in small proportions (approx. 2%).

Commercial polyvinyl alcohols are supplied as white-yellowish powders or granules having degrees of polymerization in the range from approx. 100 to 2500 (molar masses of from approx. 4000 to 100 000 g/mol). The polyvinyl alcohols are characterized on the part of the manufacturers by specifying the degree of polymerization of the starting polymer, the degree of hydrolysis, the hydrolysis number and the solution viscosity.

Depending on the degree of hydrolysis, polyvinyl alcohols are soluble in water and a few strongly polar organic solvents (formamide, dimethylformamide, dimethyl sulfoxide); they are not attacked by (chlorinated) hydrocarbons, esters, fats and oils. Polyvinyl alcohols are classified as being toxicologically uncontroversial and are at least partly biodegradable. The solubility in water can be reduced by aftertreatment with aldehydes (acetalization), by complexation with Ni or Cu salts or by treatment with dichromates, boric acid or borax. The coatings made of polyvinyl alcohol are substantially impenetrable to gases such as oxygen, nitrogen, helium, hydrogen, carbon dioxide, but allow water vapor to pass through.

The materials which are used for the container are preferably polyvinyl alcohols of a certain molecular weight range, preference being given in accordance with the invention to the water-soluble or water-dispersible container comprising a polyvinyl alcohol whose molecular weight is in the range of from 10 000 to 100 000 gmol$^{-1}$, preferably of from 11 000 to 90 000 gmol$^{-1}$, more preferably of from 12 000 to 80 000 gmol$^{-1}$ and in particular of from 13 000 to 70 000 gmol$^{-1}$.

In a particularly preferred embodiment of the present invention, the polymeric carrier material of the particles consists at least proportionally of ethylene/vinyl acetate copolymer. The present application therefore further preferably provides a fragrance release system, characterized in that the polymeric carrier material contains at least 10% by weight, preferably at least 30% by weight, more preferably at least 70% by weight, of ethylene/vinyl acetate copolymer, and is preferably produced fully from ethylene/vinyl acetate copolymer.

Ethylene/vinyl acetate copolymers is the term for copolymers made of ethylene and vinyl acetate. This polymer is in principle prepared in a process comparable to the preparation of polyethylene of low density (LDPE; low-density polyethylene). With an increasing proportion of vinyl acetate, the crystallinity of the polyethylene is disrupted and the melting and softening points and the hardness of the resulting products are lowered in this way. The vinyl acetate additionally makes the copolymer more polar and thus improves its adhesion to polar substrates.

The above-described ethylene/vinyl acetate copolymers are commercially widely available, for example under the trademark Elvax® (Dupont). Particularly suitable polyvinyl alcohols in the context of the present invention are, for example, Elvax® 265, Elvax® 240, Elvax® 205 W, Elvax® 200 W and Elvax® 360.

Some particularly suitable copolymers and their physical properties can be taken from the table below:

| Product name | % by weight of vinyl acetate (based on the total weight) | Melting point |
| --- | --- | --- |
| Elvax ® 40W | 40 | 47° C. |
| Elvax ® 150 | 33 | 63° C. |
| Elvax ® 265 | 28 | 75° C. |
| Elvax ® 240 | 28 | 74° C. |
| Elvax ® 205 W | 28 | 72° C. |
| Elvax ® 200 W | 28 | 71° C. |
| Elvax ® 360 | 25 | 78° C. |
| Elvax ® 460 | 18 | 88° C. |
| Elvax ® 660 | 12 | 96° C. |
| Elvax ® 760 | 9 | 100° C. |

In the context of the present invention, especially in the field of fragrancing the interiors of machine dishwashers, particular preference is given to fragrance release systems in which the polymeric carrier material used is ethylene/vinyl acetate copolymer and this copolymer contains from 5 to 50% by weight of vinyl acetate, preferably from 10 to 40% by weight of vinyl acetate and in particular from 20 to 30% by weight of vinyl acetate, based in each case on the total weight of the copolymer.

Inventive fragrance release systems comprise the polymeric carrier materials in the form of particles. The three-dimensional shape of these particles is restricted merely by the technical possibilities in their production. Possible three-dimensional shapes are all embodiments which can be handled viably, i.e., for example, cubes, cuboids and corresponding three-dimensional elements having flat side surfaces, and also in particular cylindrical embodiments with circular or oval cross section. This last embodiment embraces tablet-shaped particles up to compact cylinder sections having a ratio of height to diameter above 1. Further possible three-dimensional shapes are spheres, hemispheres or "stretched spheres" in the form of ellipsoidal capsules, as are regular polyhedra, for example tetrahedra, hexahedra, octahedra, dodecahedra, icosahedra. Also conceivable are star-shaped embodiments with three, four, five, six or more points or fully irregular bodies which can be configured, for example, in a motif. Suitable motifs, depending upon the field of use of the inventive compositions are, for example, animal figures such as dogs, horses or birds, floral motifs or the illustration of fruits. However, the motif-type embodiment may also relate to inanimate objects such as vehicles, tools, household objects or clothing. The surface of the solid particles may have unevenness depending upon the type of production process selected and/or a selected coating. Owing to the numerous possible embodiments of the particles, the inventive compositions are notable for advantages not only in their production. Owing to the numerous embodiment forms, the fragrance-containing particles are additionally clearly perceptible visually to the consumer and enable, by the selective spatial configuration of these particles, a visualization, particularly advantageous for product acceptance, of the fragrances present in the inventive compositions or further active substances optionally present in these compositions. For instance, the visually perceptible multiphasicity of these compositions may illustrate, for example, the differing function of individual active substances (for example cleaning and additional functions such as glass protection, silver protection, etc.).

In the context of the present application, particles have a solid consistency at room temperature, i.e. dimensionally stable and not free-flowing. Preferred particles have an average diameter of from 0.5 to 20 mm, preferably of from 1 to 10 mm and in particular of from 3 to 6 mm.

The polymeric carrier materials can be formulated to give the above-described particles by all processes known to those skilled in the art for the processing of these substances. Preference is given in the context of the present invention to extrusion, injection molding and spraying to give polymer granules.

In addition to a vessel, inventive fragrance release systems also comprise fragrance-containing particles based on polymeric carrier materials, the proportion by weight of the fragrance(s), based on the total weight of the particles, being preferably from 1 to 70% by weight, preferably from 10 to 60% by weight, more preferably from 20 to 50% by weight, in particular from 30 to 40% by weight.

In the context of the present invention, the perfume oils or fragrances used may be individual odorant compounds, for example the synthetic products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether; the aldehydes include, for example, the linear alkanals having from 8 to 18 carbon atoms, citral, citronellal, citronellyloxyacetaldehyde, cyclamen aldehyde, hydroxycitronellal, lilial and bourgeonal; the ketones include, for example, the ionones, α-isomethylionone and methyl cedryl ketone; the alcohols include anethol, citronellol, eugenol, geraniol, linalool, phenylethyl alcohol and terpineol; the hydrocarbons include primarily the terpenes, such as limonene and pinene. However, preference is given to using mixtures of different odorants which together generate a pleasing fragrance note. Such perfume oils may also contain natural odorant mixtures, as obtainable from vegetable sources, e.g. pine oil, citrus oil, jasmine oil, patchouli oil, rose oil and ylang-ylang oil. Likewise suitable are muscatel, sage oil, chamomile oil, oil of cloves, *melissa* oil, mint oil, cinnamon leaf oil, lime blossom oil, juniperberry oil, vetiver oil, olibanum oil, galbanum oil and labdanum oil, and orange blossom oil, neroliol, orange peel oil and sandalwood oil.

The general description of the perfumes which can be used (see above) is a general representation of the different classes of odorant substances. In order to be perceptible, an odorant must be volatile, for which an important role is played not only by the nature of the functional groups and by the structure of the chemical compound but also by the molar mass. Thus, the majority of odorants have molar masses of up to about 200 daltons, while molar masses of 300 daltons or more tend to be an exception. On the basis of the different volatility of odorants there is a change in the odor of a perfume or fragrance composed of two or more odorants during its evaporation, and the perceived odors are divided into top note, middle note or body, and end note or dryout. Since the perception of odor is to a large extent also based on the odor intensity, the top note of a perfume or fragrance mixture does not consist only of volatile compounds, whereas the base note consists for the most part of less volatile odorants, i.e., odorants which adhere firmly. In the composition of perfumes it is possible for more volatile odorants, for example, to be bound to certain fixatives, which prevent them from evaporating too rapidly. The subsequent classification of the odorants into "more volatile" and "firmly adhering" odorants, therefore, states nothing about the perceived odor and about whether the odorant in question is perceived as a top note or as a middle note.

An appropriate selection of the fragrances and perfume oils mentioned can in this way allows both the product odor directly on opening the brand new composition and the use fragrance, for example when used in a machine dishwasher, for the inventive composition to be influenced. These perceived fragrances may of course be the same but they may also be different. It is advantageous to use more firmly adhering odorants for the latter perceived odor, while more volatile odorants can also be used to fragrance the product. Examples of firmly adhering odorants which can be used in the context of the present invention are the essential oils such as *angelica* root oil, anise oil, *arnica* blossom oil, basil oil, bay oil, bergamot oil, champaca blossom oil, noble fir oil, noble fir cone oil, elemi oil, *eucalyptus* oil, fennel oil, spruce needle oil, galbanum oil, *geranium* oil, ginger grass oil, guaiacwood oil, gurjun balsam oil, *helichrysum* oil, ho oil, ginger oil, iris oil, cajeput oil, *calamus* oil, chamomile oil, camphor oil, *canaga* oil, cardamom oil, *cassia* oil, pine needle oil, copaiva balsam oil, coriander oil, spearmint oil, caraway oil, cumin oil, lavender oil, lemon grass oil, lime oil, mandarin oil, *melissa* oil, musk seed oil, myrrh oil, oil of cloves, neroli oil, niaouli oil, olibanum oil, orange oil, *origanum* oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, turpentine oil, *thuja* oil, thyme oil, *verbena* oil, vetiver oil, juniperberry oil, wormwood oil, wintergreen oil, ylang-ylang oil, hyssop oil, cinnamon oil, cinnamon leaf oil, citronellol, lemon oil and cypress oil. However, the higher-boiling or solid odorants of natural or synthetic origin may also be used in the context of the present invention as firmly adhering odorants or odorant mixtures, i.e. fragrances. These compounds include the following compounds and mixtures thereof: ambrettolide, α-amylcinnamaldehyde, anethole, anisaldehyde, anisyl alcohol, anisole, methyl anthranilate, acetophenone, benzylacetone, benzaldehyde, ethyl benzoate, benzophenone, benzyl alcohol, benzyl acetate, benzyl benzoate, benzyl formate, benzyl valerate, borneol, bornyl acetate, α-bromostyrene, n-decyl aldehyde, n-dodecylaldehyde, eugenol, eugenol methyl ether, eucalyptol, farnesol, fenchone, fenchyl acetate, geranyl acetate, geranyl formate, heliotropin, methyl heptynecarboxylate, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methyl methylanthranilate, p-methylacetophenone, methylchavicol, p-methylquinoline, methyl β-naphthyl ketone, methyl-n-nonylacetaldehyde, methyl n-nonyl ketone, muscone, β-naphthol ethyl ether, β-naphthol methyl ether, nerol, nitrobenzene, n-nonylaldehyde, nonyl alcohol, n-octylaldehyde, p-oxyacetophenone, pentadecanolide, β-phenylethyl alcohol, phenylacetaldehyde dimethyl acetal, phenylacetic acid, pulegone, safrol, isoamyl salicylate, methyl salicylate, hexyl salicylate, cyclohexyl salicylate, santalol, skatole, terpineol, thymene, thymol, γ-undecalactone, vanillin, veratrum aldehyde, cinnamaldehyde, cinnamyl alcohol, cinnamic acid, ethyl cinnamate, benzyl cinnamate. The more volatile odorants include in particular the lower-boiling odorants of natural or synthetic origin, which may be used alone or in mixtures. Examples of more volatile odorants are alkyl isothiocyanates (alkyl mustard oils), butanedione, limonene, linalool, linalyl acetate and linalyl propionate, menthol, menthone, methyl-n-heptenone, phellandrene, phenylacetaldehyde, terpinyl acetate, citral, citronellal.

Preference is given to loading the plastics particles with the selected fragrance at a temperature of from 15 to 30° C., preferably of from 20 to 25° C. To this end, the particles are admixed with the appropriate amount of the fragrance and mixed. In any case, the temperature should, though, be below the melting or decomposition temperature of the plastic and also below the flashpoint of the perfume oil. The fragrance is absorbed by the polymeric carrier material or by further perfume carrier materials present in the particles primarily by adhesion, diffusion and/or capillary forces, and the particles may swell slightly in the course of this operation.

As mentioned above, inventive compositions may comprise, apart from the constituents needed for fragrancing and deodorization, further active substances. It is accordingly possible to distinguish, from the compositions which serve exclusively for fragrancing, further product groups which, in addition to the aforementioned inventive constituents, comprise further preferred substances.

A first of these optionally usable preferred substances is the dyes. Suitable for this purpose are generally all dyes which are known by those skilled in the art to be suitable for coloring plastics and to be soluble in perfume oils. Preference is given to selecting the dye according to the fragrance used; for example, particles having a lemon fragrance preferably have a yellow color, while preference is given to a green color for particles having an apple or herb fragrance. Preferred dyes have high storage stability and insensitivity toward the remaining ingredients of the compositions and to light. When the inventive compositions are used in connection with textile cleaning or dishwashing, the dyes used should not have any marked substantivity toward textile fibers, glass, plasticware or ceramics, in order not to stain them.

Suitable dyes and dye mixtures are commercially available under various trade names and are supplied by firms including BASF AG, Ludwigshafen, Bayer AG, Leverkusen, Clariant GmbH, DyStar Textilfarben GmbH & Co. Deutschland KG, Les Colorants Wackherr SA and Ciba Specialty Chemicals. The suitable fat-soluble dyes and dye mixtures include, for example, Solvent Blue 35, Solvent Green 7, Solvent Orange 1 (Orange au Gras-W-2201), Sandoplast Blau 2B, Fettgelb 3G, Iragon® Red SRE 122, Iragon® Green SGR 3, Solvent Yellow 33 and Solvent Yellow 16, but other dyes may also be present.

In a preferred embodiment, the dye, in addition to its esthetic effect, additionally has an indicator function. This indicates to the consumer the actual consumption level of the deodorant, so that he/she obtains, in addition to the absence of fragrance impression which may, for example, be based on an accustoming effect on the part of the user, a further reliable indication as to when the deodorant should be replaced by a new one.

The indicator effect may be achieved in various ways: one way is to use a dye which escapes from the particles in the course of the use time. This may be brought about, for example, by the ingredients present in the dishwasher detergent. To this end, a dye has to be used which adheres well to the particles and only slowly diffuses out of them, in order to ensure that the discoloration is not complete too early, i.e. when the fragrance has not yet been consumed. Another way is that a color change is brought about by a chemical reaction or thermal decomposition.

Further preferred constituents of inventive compositions are substances such as active antimicrobial ingredients, germicides, fungicides, antioxidants or corrosion inhibitors, with the aid of which additional uses, for example disinfection or corrosion protection, can be realized.

For the control of microorganisms, the inventive compositions may comprise active antimicrobial ingredients. Depending on the antimicrobial spectrum and mechanism of action, a distinction is drawn between bacteriostats and bacteriocides, fungistats and fungicides, etc. Important substances from these groups are, for example, benzalkonium chlorides, alkylarylsulfonates, halophenols and phenylmercuric acetate.

In order to prevent undesired changes, caused by the action of oxygen and other oxidative processes, to the inventive compositions or to the treated, for example textiles, the compositions may comprise antioxidants. This compound class includes, for example, substituted phenols, hydroquinones, pyrocatechols, and aromatic amines, and also organic sulfides, polysulfides, dithiocarbamates, phosphites and phosphonates.

When the inventive compositions are used in machine dishwashers, these compositions may comprise corrosion inhibitors to protect the ware or the machine, and particularly silver protectants have special significance in the field of machine dishwashing. It is possible to use the known substances of the prior art. Generally, it is possible in particular to use silver protectants selected from the group of the triazoles, the benzotriazoles, the bisbenzotriazoles, the aminotriazoles, the alkylaminotriazoles and the transition metal salts or complexes. Particular preference is given to using benzotriazole and/or alkylaminotriazole. Frequently also found in cleaning formulations are active chlorine-containing agents which can significantly reduce the corrosion of the silver surface. In chlorine-free detergents, particularly oxygen- and nitrogen-containing organic redox-active compounds, such as di- and trihydric phenols, for example hydroquinone, pyrocatechol, hydroxyhydroquinone, gallic acid, phloroglucine, pyrogallol and derivatives of these classes of compound, are used. Salt- and complex-type inorganic compounds, such as salts of the metals Mn, Ti, Zr, Hf, V, Co and Ce, also frequently find use. Preference is given in this context to the transition metal salts which are selected from the group of manganese and/or cobalt salts and/or complexes, more preferably cobalt(ammine) complexes, cobalt(acetate) complexes, cobalt(carbonyl) complexes, the chlorides of cobalt or manganese, and manganese sulfate. Zinc compounds may likewise be used to prevent corrosion on the ware.

Instead of or in addition to the above-described silver protectants, for example the benzotriazoles, it is possible to use redox-active substances in the inventive compositions. These substances are preferably inorganic redox-active substances from the group of the manganese, titanium, zirconium, hafnium, vanadium, cobalt and cerium salts and/or complexes, the metals preferably being in one of the oxidation states II, III, IV, V or VI.

The metal salts or metal complexes used should be at least partially soluble in water. The counterions suitable for the salt formation include all customary singly, doubly or triply negatively charged inorganic anions, for example oxide, sulfate, nitrate, fluoride, but also organic anions, for example stearate.

Metal complexes in the context of the invention are compounds which consist of a central atom and one or more ligands, and optionally additionally one or more of the abovementioned anions. The central atom is one of the abovementioned metals in one of the abovementioned oxidation states. The ligands are neutral molecules or anions which are mono- or polydentate; the term "ligands" in the context of the invention is explained in more detail, for example, in "Römpp Chemie Lexikon, Georg Thieme Verlag, Stuttgart/New York, 9th edition, 1990, page 2507". When the charge of the central atom and the charge of the ligand(s) within a metal complex do not add up to zero, depending on whether there is a cationic or an anionic charge excess, either one or more of the abovementioned anions or one or more cations, for example sodium, potassium, ammonium ions, ensure that the charge balances. Suitable complexing agents are, for example, citrate, acetyl acetonate or 1-hydroxyethane-1,1-diphosphonate.

The definition of "oxidation state" customary in chemistry is reproduced, for example, in "Römpp Chemie Lexikon, Georg Thieme Verlag, Stuttgart/New York, 9th edition, 1991, page 3168".

Particularly preferred metal salts and/or metal complexes are selected from the group of $MnSO_4$, Mn(II) citrate, Mn(II) stearate, Mn(II) acetylacetonate, Mn(II) [1-hydroxyethane-1, 1-diphosphonate], $V_2O_5$, $V_2O_4$, $VO_2$, $TiOSO_4$, $K_2TiF_6$, $K_2ZrF_6$, $COSO_4$, $Co(NO_3)_2$, $Ce(NO_3)_3$, and mixtures thereof, so that preferred inventive compositions are characterized in that the metal salts and/or metal complexes are selected from the group of $MnSO_4$, Mn(II) citrate, Mn(II) stearate, Mn(II) acetylacetonate, Mn(II) [1-hydroxyethane-1, 1-diphosphonate], $V_2O_5$, $V_2O_4$, $VO_2$, $TiOSO_4$, $K_2TiF_6$, $K_2ZrF_6$, $COSO_4$, $Co(NO_3)_2$, $Ce(NO_3)_3$.

These metal salts or metal complexes are generally commercial substances which can be used in the inventive compositions for the purposes of silver corrosion protection without prior purification. For example, the mixture of penta- and tetravalent vanadium ($V_2O_5$, $VO_2$, $V_2O_4$) known from the preparation of $SO_3$ (contact process) is therefore suitable, as is the titanyl sulfate $TiOSO_4$ which is obtained by diluting a $Ti(SO_4)_2$ solution.

The metal salts and/or metal complexes mentioned are present in the inventive compositions preferably in an amount of from 0.05 to 6% by weight, preferably from 0.2 to 2.5% by weight, based on the overall composition without the container.

A further important criterion for the assessment of a machine dishwasher detergent is, aside from its cleaning performance, the visual appearance of the dry dishes on completion of cleaning. Any calcium carbonate deposits which arise on dishes or in the interior of the machine might, for example, impair customer satisfaction and thus have a causal influence on the economic success of such a detergent. A further problem which has existed for some time in machine dishwashing is the corrosion of glassware, which can usually manifest itself by the appearance of clouding, smearing and scratches, but also by an iridescence of the glass surface. The observed effects are based essentially on two operations, firstly the exit of alkali metal and alkaline earth metal ions from the glass in conjunction with a hydrolysis of the silicate network, and secondly in a deposition of silicatic compounds on the glass surface.

The problems mentioned can be solved using the inventive compositions when, in addition to the aforementioned obligatory and any optional ingredients, certain glass corrosion inhibitors are incorporated into the compositions. Preferred inventive compositions therefore additionally comprise one or more magnesium and/or zinc salts and/or magnesium and/or zinc complexes.

A preferred class of compounds which can be added to the inventive compositions to prevent glass corrosion is that of insoluble zinc salts. These can position themselves during the dishwashing operation on the glass surface, where they prevent metal ions from the glass network from going into solution, and also the hydrolysis of the silicates. Additionally, these insoluble zinc salts also prevent the deposition of silicate on the surface of the glass, so that the glass is protected from the consequences outlined above.

In the context of this preferred embodiment, insoluble zinc salts are zinc salts which have a maximum solubility of 10 grams of zinc salt per liter of water at 20° C. Examples of insoluble zinc salts which are particularly preferred in accordance with the invention are zinc silicate, zinc carbonate, zinc oxide, basic zinc carbonate ($Zn_2(OH)_2CO_3$), zinc hydroxide, zinc oxalate, zinc monophosphate ($Zn_3(PO_4)_2$), and zinc pyrophosphate ($Zn_2(P_2O_7)$).

The zinc compounds mentioned are used in the inventive compositions in amounts which bring about a content in the compositions of zinc ions of between 0.02 and 10% by weight, preferably between 0.1 and 5.0% by weight and in particular between 0.2 and 1.0% by weight, based in each case on the composition without the container. The exact content in the compositions of zinc salt or zinc salts is by its nature dependent on the type of the zinc salts—the less soluble the zinc salt used, the higher its concentration in the inventive compositions should be.

A further preferred class of compounds is that of magnesium and/or zinc salt(s) of at least one monomeric and/or polymeric organic acid. These have the effect that, even upon repeated use, the surfaces of glassware are not altered as a result of corrosion, and in particular no clouding, smears or scratches, and also no iridescence of the glass surfaces, are caused.

Even though all magnesium and/or zinc salt(s) of monomeric and/or polymeric organic acids may be present in accordance with the invention in the claimed compositions, preference is given, as described above, to the magnesium and/or zinc salts of monomeric and/or polymeric organic acids from the groups of the unbranched, saturated or unsaturated monocarboxylic acids, the branched, saturated or unsaturated monocarboxylic acids, the saturated and unsaturated dicarboxylic acids, the aromatic mono-, di- and tricarboxylic acids, the sugar acids, the hydroxy acids, the oxo acids, the amino acids and/or the polymeric carboxylic acids. In the context of the present invention, preference is in turn given within these groups to the acids specified below:

The spectrum of the zinc salts, preferred in accordance with the invention, of organic acids, preferably of organic carboxylic acids, ranges from salts which are sparingly soluble or insoluble in water, i.e. have a solubility below 100 mg/l, preferably below 10 mg/l, in particular have zero solubility, to those salts which have a solubility in water above 100 mg/l, preferably above 500 mg/l, more preferably above 1 g/l and in particular above 5 g/l (all solubilities at water temperature 20° C.). The first group of zinc salts includes, for example, zinc citrate, zinc oleate and zinc stearate; the group of soluble zinc salts includes, for example, zinc formate, zinc acetate, zinc lactate and zinc gluconate.

In a further preferred embodiment of the present invention, the compositions according to the invention comprise at least one zinc salt, but no magnesium salt of an organic acid, preferably at least one zinc salt of an organic carboxylic acid, more preferably a zinc salt from the group of zinc stearate, zinc oleate, zinc gluconate, zinc acetate, zinc lactate and/or zinc citrate. Preference is also given to zinc ricinoleate, zinc abietate and zinc oxalate.

A composition which is preferred in the context of the present invention contains zinc salt in amounts of from 0.1 to 5% by weight, preferably from 0.2 to 4% by weight and in particular from 0.4 to 3% by weight, or zinc in oxidized form (calculated as $Zn^{2+}$) in amounts of from 0.01 to 1% by weight, preferably from 0.02 to 0.5% by weight and in particular from 0.04 to 0.2% by weight, based in each case on the composition without the container.

The present application therefore further provides a fragrance release system which comprises further active substances, in particular active substances from the group of the perfume carriers, dyes, active antimicrobial ingredients, germicides, fungicides, antioxidants or corrosion inhibitors.

BRIEF DESCRIPTION OF THE DRAWINGS

The invention is illustrated in detail by way of example with reference to the drawing. In the drawing.

DETAILED DESCRIPTION OF THE DRAWINGS

Figure 1:
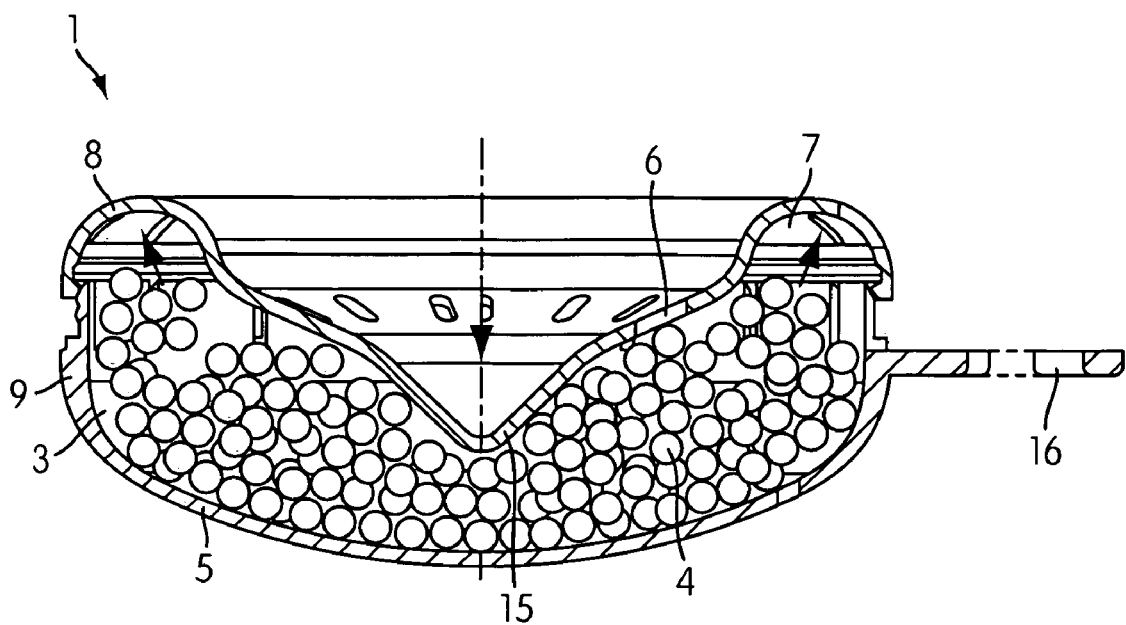
FIG. 1 shows an inventive fragrance release system in cross section after the introduction of the particles and before the closure of the container.

A fragrance release system indicated generally by 1 has a substantially rotationally symmetric container indicated generally by 2 having an accommodation chamber 3 and a multitude of particles 4, accommodated in the accommodation chamber 3 of the container 2, for deodorizing and/or fragrancing of closed spaces, in particular the interiors of machine dishwashers.

The particles 4 have a carrier material, preferably made of a polymer, and also at least one fragrance, and preferably have a melting or softening point between 30° and 150° C., in particular 75° C. and 80° C. Preferred materials for the particles 4 are described in detail in the German patent application 102 37 066.4 which has an earlier priority date but had not been published at the priority date of the present application, which is explicitly incorporated by reference to avoid repetitions and whose disclosure content is incorporated into the disclosure content of this application.

Essential for the nventive fragrance release system 1 is the configuration of the container 2. As is best evident from FIGS. 1 to 3, the accomodation chamber 3 of the container has a crescent-like cross-sectional shape with a convex front wall 5 and a concave back wall portion 6, outside the conelike middle region 15, the two end regions 7 of the crescent-like cross-sectional shape of the accommodation chamber 3 being rounded.

This container 2 may have a one-part configuration and be produced, for example, by blow molding; in that case, a filling orifice for the particles 4 has to be provided and is closed after the particles 4 have been introduced.

However, preference is given to providing, as shown in the working examples, that the container 2 has a two-part configuration, one part 2' having the back wall 6 and the other part 2" having the front wall 5.

The part 2', having the back wall 6, of the container 2 also has a bulge-like edge region 8 which can be connected to a strut-like edge region 9 of the other part 2", a snap-in connection preferably being provided for the connection. For instance, in the working example, a snap-in bead 10 is provided on the strut-like edge region 9 and a snap-in lug 11 on the interior of the bulge-like edge region 8.

In the region of the convex front wall 5, the container 2 has a multitude of orifices 12, through which the emission of the fragrances of the particles 4 from the accommodation chamber 3 outward is possible. In addition, a multitude of slot-shaped orifices 13 and 14 are present in the region of the back wall 6 and in the region of the bulge-like edge region 8.

In the two-part configuration of the container 2 shown, it is also provided for simplification of the filling operation outlined below that the concave back wall 6 curves inward in a conelike manner in its middle region 15.

In a preferred embodiment the fragrance release system 1 consists of perfumed polymer particles (e.g. ethylene/vinyl acetate copolymer) enclosed in a perforated container 2 (for example made of propylene) The polymer particles may be formed, for example, by Elvax® 265 from Dupont having a melting point of 75° C., which can take up from about 25 to 30% perfume oil at room temperature. This granule is a common raw material for the plastics processing industry and is readily available. The fact that these particles can be laden with perfume oil at low temperature and combustion of the perfume oil can be avoided makes these particles particularly suitable for use in an inventive fragrance release system. The radius of the particles 4 is from about 1.5 to 3 mm and enables rapid economic loading with perfume oil.

Both parts 2', 2" of the container 2 are preferably produced from polypropylene in an injection molding process; one of the two parts 2', 2" has on its exterior a hook 16 for hanging on a basket of a dishwasher or the like. The container parts 2', 2" may also be produced in another manner or consist of other plastics materials, as laid out in detail in the German patent application 102 37 066.4 which has an earlier priority date but had not been published at the priority date of the present application, to which reference is explicitly made.

While the orifices 12 in the front wall 5 serve primarily for the emission of the perfume oil from the particles 4 outward, for example into the interior of a machine dishwasher, the preferably slot-shaped orifices 13, 14 on the back wall 6 of the container are provided to enable water to run in and out in the course of the washing operation, in order to improve the fragrance release.

Figure 2:
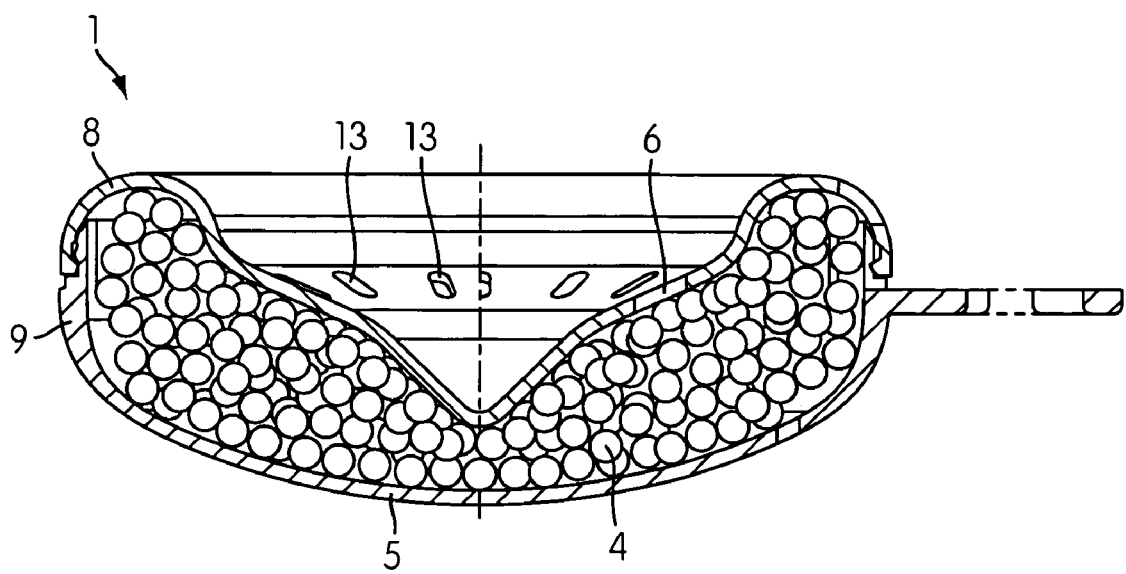
FIG. 2 shows a fragrance release system as per FIG. 1 after the closure of the container.
Figure 3:
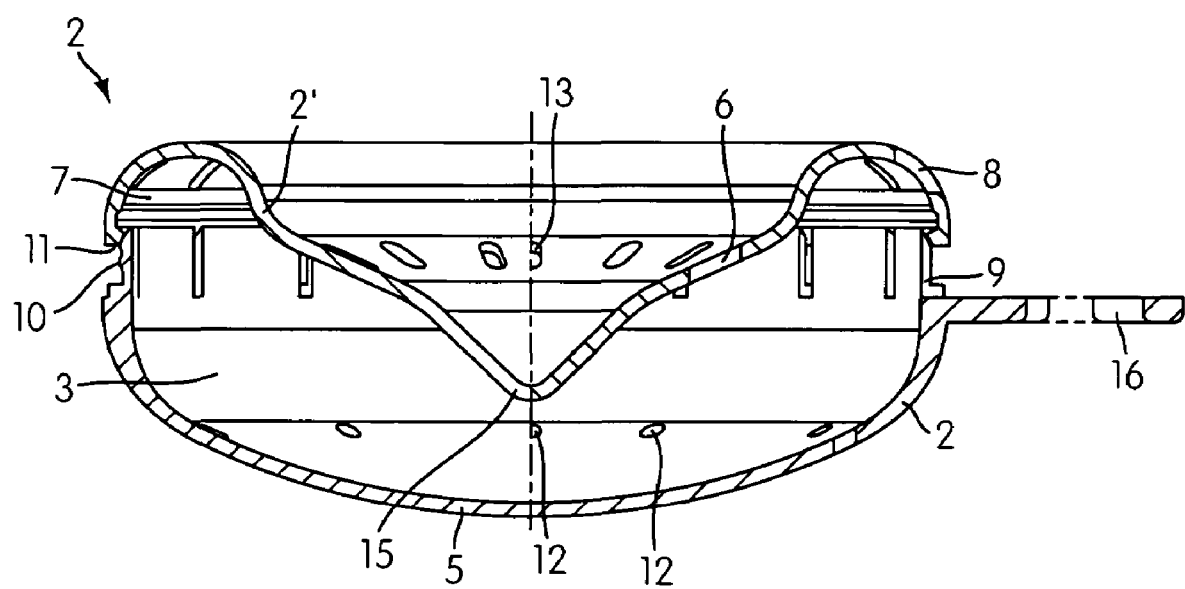
FIG. 3 shows a cross section through the container of the fragrance release system.
Figure 4:
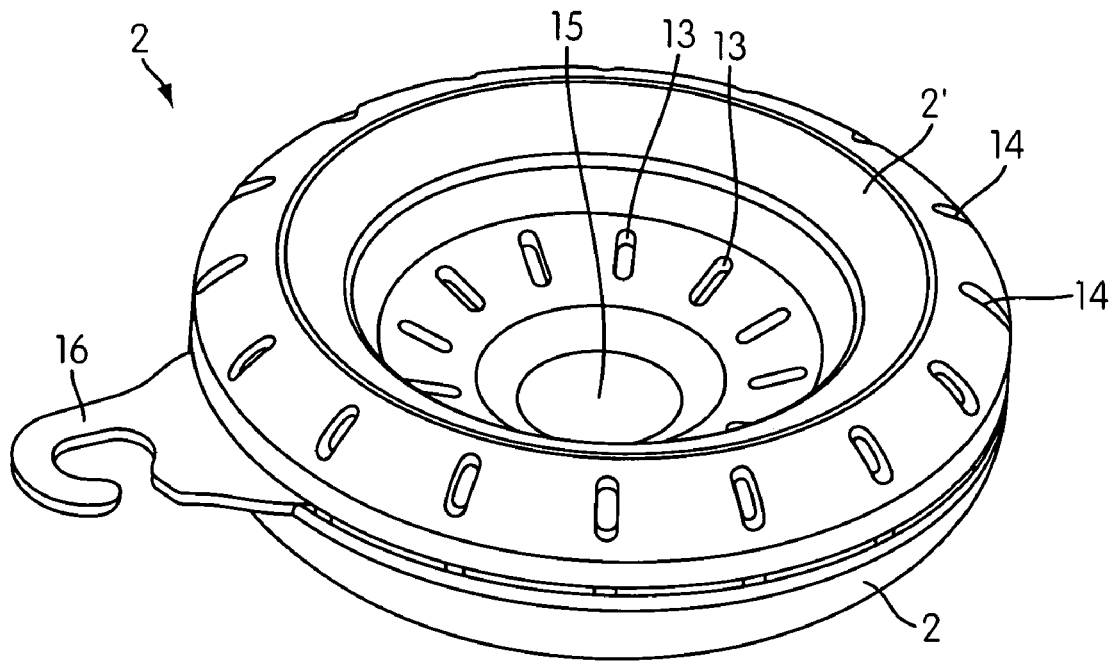
FIG. 4 shows the closed container of the fragrance release system in perspective representation in back view.
Figure 5:
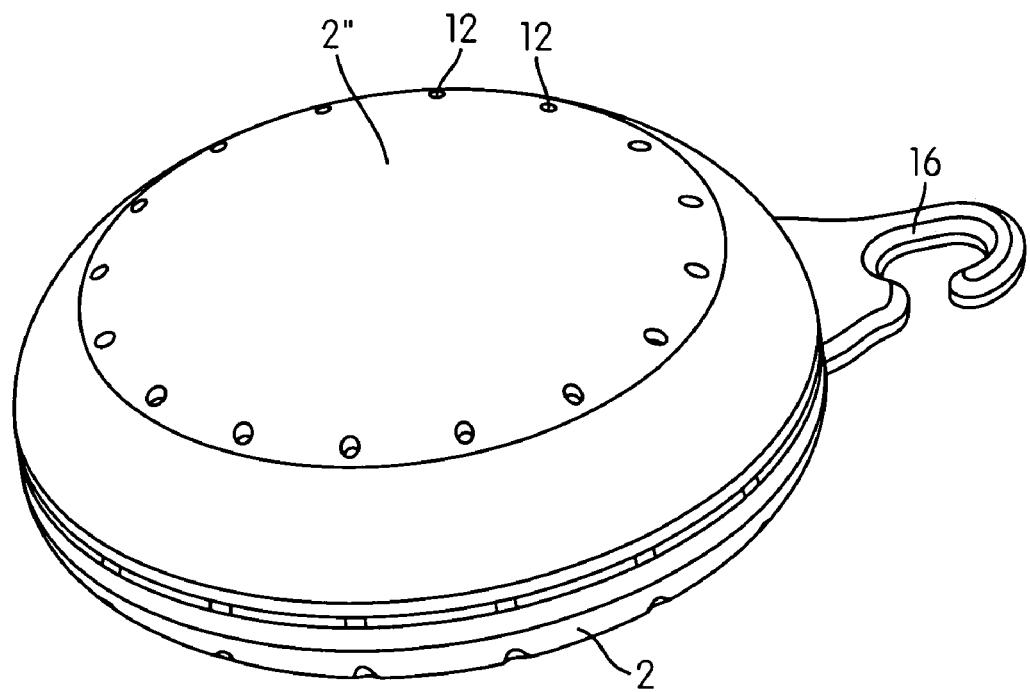
FIG. 5 shows the container as per FIG. 4, likewise in perspective representation, in front view.

The accommodation chamber 3 of the container 2 has, for example, a volume of 40 ml, with a height and, following therefrom, a layer thickness of the particles 4 between about 10 and 12 mm. This accommodation chamber 3 is, as shown in FIGS. 1 and 2, filled fully with particles 4. In the filling position (FIG. 1), the part 2" having the front wall 5 forms the actual receptacle of the container 2, while the part 2' having the back wall 6 constitutes a kind of lid.

The required amount of particles 4 is initially introduced into the part 2", in such a way that the fill level remains somewhat below the upper edge of the strut-like edge region 9. Subsequently, the part 2' is laid on and lowered (large arrow in FIG. 1). About the first third of the concave back wall 6 with conical middle region 15 is immersed into the particles 4 and displaces some particles 4 to the periphery of the container 2 and upward. Before the particles 4 reach the upper edge, the bulge-like edge region 8 of the container part 2' reaches the strut-like edge region 9 of the part 2" and the particles 4 cannot fall out out of the container 2. The further lowering of the part 2' (FIG. 1, large arrow) brings about the immersion of the further part of the conical middle region 15, which leads to particles being displaced from the peripheral region upward into the still-empty region of the accommodation chamber 3 (small arrows in FIG. 1), which results in this region of the accommodation chamber 3 being filled fully. When this occurs, the two parts 2', 2" snap into one another owing to the snap-in connection 9, 10, and the container 2 is closed permanently. In the case of a precise metered amount of particles 4, the container 2 is thus filled fully, as shown in FIG. 2.

The particles 4 are thus not arranged loosely in the container 2 and, after the first washing operation in a dishwasher, they form a crescent-like conglomerate having a layer thickness of from 10 to 12 mm as a result of attainment of their softening temperature, which reduces the exposed surface area of the particles 4 and enables a long functionality of the system. In contrast, if the particles 4 were to be freely mobile within the container 2, the functioning time of the fragrance release system would be dependent only upon the amount of perfume oil which is present in each particle 4; the number of particles 4 would only influence the fragrance intensity.

The inventive configuration of the fragrance release system thus reduces the exposed surface area of the particles 4, so that not all particles can release their fragrance at once; the fragrance intensity is thus determined by the amount of particles at the surface of the conglomerate in direct contact with the air, but not by all particles. The perfume oil from the inner particles migrates progressively to the surface of the conglomerate; the inner particles thus play a depot function for the fragrance release system and thereby enable a substantially longer functioning time of the system. It has been found that 50 washing operations at approx. 3 to 4 wash cycles per week using such a fragrance release system in a machine dishwasher are quite possible without impairment of function.

The special design of the container 2 of the fragrance release system 1 allows a particularly favorable ratio of the total surface area of all particles 4 in the starting state (before they have been heated for the first time, for example in a wash operation) to the total surface area of the accommodation chamber to be achieved. For instance, a volume of the accommodation chamber 3 of 40 ml results in a total particle surface area of approx. 250 $cm^2$ with the assumption that the particles 4 are approximately spherical and have an average radius of 2 mm. The interior surface area of the accommodation chamber 3 of the casing is about 88.5 cm², so that it can be assumed that the particle conglomerate in the closed container likewise has a total surface area of 88.5 cm². This gives a ratio between the total surface area of all particles in the starting state to the total surface area of the accommodation chamber of 1:0.353 (approximate value) as the optimal value for the fragrance release system to ensure effective fragrance release at low container volume.

In contrast, if the particles were to be enclosed in a spherical casing of the same volume (40 ml), the interior surface area of this sphere would be 56.8 cm². This would give a ratio of 1:0.227. However, such an embodiment of the container 2 has been found to be unfavorable, because the fragrant surface area of the particles 4 is too small and the fragrance intensity decreases too greatly as a result.

The above-described processes for designing the containers of inventive compositions will generally be directed just as much by visual considerations as the ultimate intended use of these compositions. The inventive compositions may, for example, in addition to the fragrance-containing particles, comprise further active substances. These active substances may be formulated within the container in a mixture or a blend with the fragrance-containing particles, or else separately from these particles. The active substances may also be incorporated into the container. These optional additional active substances may be used either in the form of an individual dose, for example for a single disinfection of a machine dishwasher, but also in the form of a multiple dosage.

In addition to the aforementioned active substances, it will be appreciated that the inventive compositions, especially compositions for use in machine dishwashers, textile washing machines or dryers, may comprise all active substances typically present in compositions for textile cleaning or dishwashing, or the care of textiles or dishes, particular preference being given to the group of the bleaches, bleach activators, polymers, builders, surfactants, enzymes, electrolytes, pH modifiers, fragrances, perfume carriers, dyes, hydrotropes, foam inhibitors, antiredeposition agents, optical brighteners, graying inhibitors, shrink preventaives, anticrease agents, dye transfer inhibitors, active antimicrobial ingredients, germicides, fungicides, antioxidants, corrosion inhibitors, antistats, repellent and impregnation agents, swelling and antislip agents, nonaqueous solvents, fabric softeners, protein hydrolyzates and UV absorbers. Such combination products are then suitable, in addition to repeated fragrancing, also for single or multiple care or cleaning of textiles or dishes.

As important constituents of detergents, the inventive compositions may comprise bleaches and bleach activators in addition to other constituents. Among the compounds which serve as bleaches and supply $H_2O_2$ in water, sodium perborate tetrahydrate and sodium perborate monohydrate are of particular significance. Further bleaches which can be used are, for example, sodium percarbonate, peroxypyrophosphates, citrate perhydrates, and $H_2O_2$-supplying peracidic salts or peracids, such as perbenzoates, peroxophthalates, diperazelaic acid, phthaloimino peracid or diperdodecanedioic acid. Detergent, tablets for machine dishwashing may also comprise bleaches from the group of organic bleaches. Typical organic bleaches are the diacyl peroxides, for example dibenzoyl peroxide. Further typical organic bleaches are the peroxy acids, particular examples being the alkyl peroxy acids and the aryl peroxy acids. Preferred representatives are (a) the peroxybenzoic acid and ring-substituted derivatives thereof, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamidoperadipic acid and N-nonenylamidopersuccinates, and, (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid and N,N-terephthaloyldi(6-aminopercaproic acid).

When the inventive compositions are used in combination with machine dishwasher detergents, they may comprise bleach activators, in order to achieve an improved bleaching action at temperatures of 60° C. and below in the course of cleaning. The bleach activators used may be compounds which, under perhydrolysis conditions, give aliphatic peroxocarboxylic acids having preferably from 1 to 10 carbon atoms, in particular from 2 to 4 carbon atoms, and/or optionally substituted perbenzoic acid. Suitable substances bear O-acyl and/or N-acyl groups of the number of carbon atoms specified, and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexa-hydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran.

Further bleach activators used with preference in the context of the present application are compounds from the group of cationic nitriles, in particular cationic nitriles of the formula

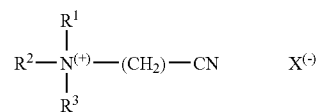

in which $R^1$ is —H, —$CH_3$, a $C_{2-24}$-alkyl or -alkenyl radical, a substituted $C_{2-24}$-alkyl or -alkenyl radical having at least one substituent from the group of —Cl, —Br, —OH, —$NH_2$, —CN, an alkyl- or alkenylaryl radical with a $C_{1-24}$-alkyl group, or is a substituted alkyl- or alkenylaryl radical having a $C_{1-24}$-alkyl group and at least one further substituent on the aromatic ring, $R^2$ and $R^3$ are each independently selected from —$CH_2$—CN, —$CH_3$, —$CH_2$—$CH_3$, —$CH_2$—$CH_2$—$CH_3$, —$CH(CH_3)$—$CH_3$, —$CH_2$—OH, —$CH_2$—$CH_2$—OH, —$CH(OH)$—$CH_3$, —$CH_2$—$CH_2$—$CH_2$—OH, —$CH_2$—$CH(OH)$—$CH_3$, —$CH(OH)$—$CH_2$—$CH_3$, —$(CH_2CH_2$—$O)_n$H where n=1, 2, 3, 4, 5 or 6 and X is an anion.

Particularly preferred inventive compositions comprise a cationic nitrile of the formula

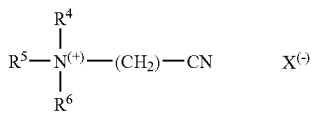

in which $R^4$, $R^5$ and $R^6$ are each independently selected from —$CH_3$, —$CH_2$—$CH_3$, —$CH_2$—$CH_2$—$CH_3$, —$CH(CH_3)$—$CH_3$, where $R^4$ may additionally also be —H and X is an anion, where preferably $R^5=R^6=$—$CH_3$ and in particular $R^4=R^5=R^6=$—$CH_3$, particular preference being given to compounds of the formulae $(CH_3)_3N^{(+)}CH_2$—CN $X^-$, $(CH_3CH_2)_3N^{(+)}CH_2$—CN $X^-$, $(CH_3CH_2CH_2)_3N^{(+)}CH_2$—CN $X^-$, $(CH_3CH(CH_3))_3N^{(+)}CH_2$—CN $X^-$, or (HO—$CH_2$—$CH_2)_3N^{(+)}CH_2$—CN $X^-$, particular preference from the group of these substances being given in turn to the cationic nitrile of the formula $(CH_3)_3N^{(+)}CH_2$—CN $X^-$ in which $X^-$ is an anion which is selected from the group of chloride, bromide, iodide, hydrogensulfate, methosulfate, p-toluenesulfonate (tosylate) or xylenesulfonate.

In addition to the conventional bleach activators, or instead of them, it is also possible to incorporate bleach catalysts into the compositions. These substances are bleach-boosting transition metal salts or transition metal complexes, for example salen or carbonyl complexes of Mn, Fe, Co, Ru or Mo. It is also possible to use Mn, Fe, Co, Ru, Mo, Ti, V and Cu complexes with N-containing tripod ligands, and also Co-, Fe-, Cu- and Ru-ammine complexes as bleach catalysts.

In addition to the bleach and bleach activator ingredients mentioned, builders are further important ingredients of detergents. The inventive compositions may comprise all builders typically used in these compositions, i.e. in particular zeolites, silicates, carbonates, organic cobuilders and, where there are no ecological prejudices against their use, also the phosphates.

Suitable crystalline, sheet-type sodium silicates have the general formula $NaMSi_xO_{2x+1} \cdot H_2O$ where M is sodium or hydrogen, x is a number from 1.9 to 4, y is a number from 0 to 20, and preferred values for x are 2, 3 or 4. Preferred crystalline sheet silicates of the formula specified are those in which M is sodium and x assumes the values 2 or 3. In particular, preference is given to both β- and also δ-sodium disilicates $Na_2Si_2O_5 \cdot yH_2O$.

It is also possible to use amorphous sodium silicates having an $Na_2O:SiO_2$ modulus of from 1:2 to 1:3.3, preferably from 1:2 to 1:2.8 and in particular from 1:2 to 1:2.6, which have retarded dissolution and secondary washing properties. The retardation of dissolution relative to conventional amorphous sodium silicates may have been brought about in a variety of ways, for example by surface treatment, compounding, compacting or by overdrying. In the context of this invention, the term "amorphous" also includes "X-ray-amorphous". This means that, in X-ray diffraction experiments, the silicates do not yield any sharp X-ray reflections typical of crystalline substances, but rather yield at best one or more maxima of the scattered X-radiation, which have a width of several degree units of the diffraction angle. However, it may quite possibly lead to even particularly good builder properties if the silicate particles in electron diffraction experiments yield vague or even sharp diffraction maxima. This is to be interpreted such that the products have microcrystalline regions with a size of from 10 to several hundred nm, and preference is given to values up to a maximum of 50 nm and in particular up to a maximum of 20 nm. Such X-ray-amorphous silicates likewise have retarded dissolution compared with conventional waterglasses. Particular preference is given to compacted amorphous silicates, compounded amorphous silicates and overdried X-ray-amorphous silicates.

The finely crystalline synthetic zeolite used, containing bound water, is preferably zeolite A and/or P. Zeolite P is particularly preferably Zeolite MAP® (commercial product from Crosfield). Also suitable, however, are zeolite X, and mixtures of A, X and/or P. Also commercially available and usable in accordance with the present invention is, for example, a cocrystal of zeolite X and zeolite A (about 80% by weight of zeolite X), which is sold by CONDEA Augusta S.p.A. under the trade name VEGOBOND AX® and can be described by the formula

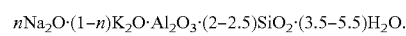

Suitable zeolites have an average particle size of less than 10 μm (volume distribution; measurement method: Coulter Counter) and preferably contain 18 to 22% by weight, in particular 20 to 22% by weight, of bound water.

It will be appreciated that it is also possible to use the commonly known phosphates as builder substances, as long as such a use should not be avoided for ecological reasons. Especially suitable are the sodium salts of the orthophosphates, of the pyrophosphates and in particular of the tripolyphosphates. To avoid repetitions, reference is made to the above remarks for a comprehensive description of these phosphates.

Organic builder substances which can be used are, for example, the polycarboxylic acids usable in the form of their alkali metal and in particular sodium salts, such as citric acid, adipic acid, succinic acid, glutaric acid, tartaric acid, sugar acids, aminocarboxylic acids, nitrilotriacetic acid (NTA), as long as such a use is not objectionable on ecological grounds, and mixtures thereof. Preferred salts are the salts of the polycarboxylic acids such as citric acid, adipic acid, succinic acid, glutaric acid, tartaric acid, sugar acids and mixtures thereof.

Further constituents which may be present are alkali metal carriers. Suitable alkali metal carriers are alkali metal hydroxides, alkali metal carbonates, alkali metal hydrogencarbonates, alkali metal sesquicarbonates, alkali metal silicates, alkali metal metasilicates, and mixtures of the substances mentioned, and preference is given in the context of this invention to the alkali metal carbonates, in particular sodium carbonate, sodium hydrogencarbonate or sodium sesquicarbonate.

When the inventive compositions are used in machine dishwashing, preference is given to water-soluble builders, since they generally have a lesser tendency to form insoluble residues on dishes and hard surfaces. Typical builders are the low molecular weight polycarboxylic acids and salts thereof, the homopolymeric and copolymeric polycarboxylic acids and salts thereof, the carbonates, phosphates and silicates. For the production of tablets for machine dishwashing, preference is given to using trisodium citrate and/or pentasodium tripolyphosphate and/or sodium carbonate and/or sodium bicarbonate and/or gluconates and/or silicatic builders from the class of the disilicates and/or metasilicates. Particular preference is given to a builder system comprising a mixture of tripolyphosphate and sodium carbonate. Particular preference is likewise given to a builder system which comprises a mixture of tripolyphosphate and sodium carbonate and sodium disilicate.

Organic cobuilders which may find use in the detergents in the context of the present invention are in particular polycarboxylates/polycarboxylic acids, polymeric polycarboxylates, aspartic acid, polyacetals, dextrins, further organic cobuilders (see below) and phosphonates. These substance classes are described below.

Organic builder substances which can be used are, for example, the polycarboxylic acids usable in the form of their sodium salts, polycarboxylic acids referring to those carboxylic acids which bear more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), as long as such a use is not objectionable on ecological grounds, and mixtures thereof. Preferred salts are the salts of the polycarboxylic acids such as citric acid, adipic acid, succinic acid, glutaric acid, tartaric acid, methylglycinediacetic acid, sugar acids and mixtures thereof.

The acids per se may also be used. In addition to their builder action, the acids typically also have the property of an acidifying component and thus also serve to set a lower and milder pH of detergents. In this connection, particular mention should be made of citric acid, succinic acid, glutaric acid, adipic acid, gluconic acid and any mixtures thereof.

Also suitable as builders are polymeric polycarboxylates; these are, for example, the alkali metal salts of polyacrylic acid or of polymethacrylic acid, for example those having a relative molecular mass of from 500 to 70 000 g/mol.

In the context of this document, the molar masses specified for polymeric polycarboxylates are weight-average molar masses $M_w$ of the particular acid form, which has always been determined by means of gel-permeation chromatography (GPC) using a UV detector. The measurement was against an external polyacrylic acid standard which, owing to its structural similarity to the polymers under investigation, provides realistic molecular weight values. These figures deviate considerably from the molecular weight data when polystyrenesulfonic acids are used as the standard. The molar masses measured against polystyrenesulfonic acids are generally distinctly higher than the molar masses specified in this document.

Suitable polymers are in particular polyacrylates which preferably have a molecular mass of from 1000 to 20 000 g/mol. Owing to their superior solubility, preference within this group may be given in turn to the short-chain polyacrylates which have molar masses of from 1000 to 10 000 g/mol and more preferably from 1200 to 4000 g/mol.

In the inventive compositions, particular preference is given to using both polyacrylates and copolymers of unsaturated carboxylic acids, monomers containing sulfonic acid groups, and optionally further ionic or nonionogenic monomers. The copolymers containing sulfonic acid groups are described in detail below.

However, it is also possible to provide inventive products which, as what are known as "3-in-1" products, combine the conventional detergents, rinse aids and a salt replacement function. For this purpose, preference is given to inventive machine dishwasher detergents which additionally contain from 0.1 to 70% by weight of copolymers of
i) unsaturated carboxylic acids
ii) sulfonic acid group-containing monomers
iii) optionally further ionic or nonionogenic monomers.

These copolymers have the effect that the dishes treated with such compositions become distinctly cleaner in the course of subsequent cleaning operations than dishes which have been washed with conventional compositions.

As an additional positive effect, a decrease in the drying time of the dishes treated with the detergent occurs, i.e. the consumer can take the dishes out of the machine sooner and reuse them after the cleaning program has finished. In the context of the inventive teaching, drying time generally refers to the literal meaning, i.e. the time which elapses before a surface of dishes treated in a machine dishwasher has dried, but in particular the time which elapses until 90% of a surface treated with a detergent or rinse aid in concentrated or dilute form has dried.

In the context of the present invention, preferred monomers are unsaturated carboxylic acids of the formula I as a monomer

$$R^1(R^2)C=C(R^3)COOH \qquad (I)$$

in which $R^1$ to $R^3$ are each independently —H, —$CH_3$, a straight-chain or branched saturated alkyl radical having from 2 to 12 carbon atoms, a straight-chain or branched, mono- or polyunsaturated alkenyl radical having from 2 to 12 carbon atoms, alkyl or alkenyl radicals as defined above and substituted by —$NH_2$, —OH or —COOH, or are —COOH or —COOR$^4$ where $R^4$ is a saturated or unsaturated straight-chain or branched hydrocarbon radical having from 1 to 12 carbon atoms.

Among the unsaturated carboxylic acids which can be described by the formula I, preference is given in particular to acrylic acid ($R^1=R^2=R^3=H$), methacrylic acid ($R^1=R^2=H$; $R^3=CH_3$) and/or maleic acid ($R^1=COOH$; $R^2=R^3=H$).

The monomers containing sulfonic acid groups are preferably those of the formula II

$$R^5(R^6)C=C(R^7)-X-SO_3H \qquad (II)$$

in which $R^5$ to $R^7$ are each independently —H, —$CH_3$, a straight-chain or branched saturated alkyl radical having from 2 to 12 carbon atoms, a straight-chain or branched, mono- or polyunsaturated alkenyl radical having from 2 to 12 carbon atoms, alkyl or alkenyl radicals as defined above and substituted by —$NH_2$, —OH or —COOH, or are —COOH or —COOR$^4$ where $R^4$ is a saturated or unsaturated, straight-chain or branched hydrocarbon radical having from 1 to 12 carbon atoms, and X is an optionally present spacer group which is selected from —$(CH_2)_n$— where n=from 0 to 4, —COO—$(CH_2)_k$— where k=from 1 to 6, —C(O)—NH—C$(CH_3)_2$— and —C(O)—NH—CH$(CH_2CH_3)$—.

Among these monomers, preference is given to those of the formulae IIa, IIb and/or IIc

$$H_2C=CH-X-SO_3H \qquad (IIa)$$

$$H_2C=C(CH_3)-X-SO_3H \qquad (IIb)$$

$$HO_3S-X-(R^6)C=C(R^7)-X-SO_3H \qquad (IIc)$$

in which $R^6$ and $R^7$ are each independently selected from —H, —$CH_3$, —$CH_2CH_3$, —$CH_2CH_2CH_3$, —$CH(CH_3)_2$ and X is an optionally present spacer group which is selected from —$(CH_2)_n$— where n=from 0 to 4, —COO—$(CH_2)_k$— where k=from 1 to 6, —C(O)—NH—C$(CH_3)_2$— and —C(O)—NH—CH$(CH_2CH_3)$—.

Particularly preferred monomers containing sulfonic acid groups are 1-acrylamido-1-propanesulfonic acid (X=—C(O) NH—CH$(CH_2CH_3)$ in formula IIa), 2-acrylamido-2-propanesulfonic acid (X=—C(O)NH—C$(CH_3)_2$ in formula IIa), 2-acrylamido-2-methyl-1-propanesulfonic acid (X=—C(O) NH—CH$(CH_3)CH_2$— in formula IIa), 2-methacrylamido-2-methyl-1-propanesulfonic acid (X=—C(O)NH—CH$(CH_3)$ CH$_2$— in formula IIb), 3-methacrylamido-2-hydroxypropanesulfonic acid (X=—C(O)NH—CH$_2$CH (OH)CH$_2$— in formula IIb), allylsulfonic acid (X=CH$_2$ in formula IIa), methallylsulfonic acid (X=CH$_2$ in formula IIb), allyloxybenzenesulfonic acid (X=—CH$_2$—O—C$_6$H$_4$— in formula IIa), methallyloxybenzenesulfonic acid (X=—CH$_2$—O—C$_6$H$_4$— in formula IIb), 2-hydroxy-3-(2-propenyloxy)propanesulfonic acid, 2-methyl-2-propene-1-sulfonic acid (X=CH$_2$ in formula IIb), styrenesulfonic acid (X=C$_6$H$_4$ in formula IIa), vinylsulfonic acid (X not present in formula IIa), 3-sulfopropyl acrylate (X=—C(O)NH—CH$_2$CH$_2$CH$_2$— in formula IIa), 3-sulfopropyl methacrylate (X=—C(O)NH—CH$_2$CH$_2$CH$_2$— in formula IIb), sulfomethacrylamide (X=—C(O)NH— in formula IIb), sulfomethylmethacrylamide (X=—C(O)NH—CH$_2$— in formula IIb) and water-soluble salts of the acids mentioned.

Useful further ionic or nonionogenic monomers are in particular ethylenically unsaturated compounds. The content of monomers of group iii) in the polymers used in accordance with the invention is preferably less than 20% by weight, based on the polymer. Polymers to be used more preferably consist only of monomers of groups i) and ii).

In summary, particular preference is given to copolymers of
i) unsaturated carboxylic acids of the formula I

R$^1$(R$^2$)C=C(R$^3$)COOH    (I)

in which R$^1$ to R$^3$ are each independently —H, —CH$_3$, a straight-chain or branched saturated alkyl radical having from 2 to 12 carbon atoms, a straight-chain or branched, mono- or polyunsaturated alkenyl radical having from 2 to 12 carbon atoms, alkyl or alkenyl radicals as defined above and substituted by —NH$_2$, —OH or —COOH, or are —COOH or —COOR$^4$ where R$^4$ is a saturated or unsaturated, straight-chain or branched hydrocarbon radical having from 1 to 12 carbon atoms, ii) monomers of the formula II containing sulfonic acid groups

R$^5$(R$^6$)C=C(R$^7$)—X—SO$_3$H    (II)

in which R$^5$ to R$^7$ are each independently —H, —CH$_3$, a straight-chain or branched saturated alkyl radical having from 2 to 12 carbon atoms, a straight-chain or branched, mono- or polyunsaturated alkenyl radical having from 2 to 12 carbon atoms, alkyl or alkenyl radicals as defined above and substituted by —NH$_2$, —OH or —COOH, or are —COOH or —COOR$^4$ where R$^4$ is a saturated or unsaturated, straight-chain or branched hydrocarbon radical having from 1 to 12 carbon atoms, and X is an optionally present spacer group which is selected from —(CH$_2$)$_n$— where n=from 0 to 4, —COO—(CH$_2$)$_k$— where k=from 1 to 6, —C(O)—NH—C(CH$_3$)$_2$— and —C(O)—NH—CH(CH$_2$CH$_3$)— iii) optionally further ionic or nonionogenic monomers.

Particularly preferred copolymers consist of
i) one or more unsaturated carboxylic acids from the group of acrylic acid, methacrylic acid and/or maleic acid,
ii) one or more monomers containing sulfonic acid groups of the formulae IIa, IIb and/or IIc:

H$_2$C=CH—X—SO$_3$H    (IIa)

H$_2$C=C(CH$_3$)—X—SO$_3$H    (IIb)

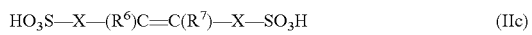
HO$_3$S—X—(R$^6$)C=C(R$^7$)—X—SO$_3$H    (IIc)

in which R$^6$ and R$^7$ are each independently selected from —H, —CH$_3$, —CH$_2$CH$_3$, —CH$_2$CH$_2$CH$_3$, —CH(CH$_3$)$_2$ and X is an optionally present spacer group which is selected from —(CH$_2$)$_n$— where n=from 0 to 4, —COO—(CH$_2$)$_k$— where k=from 1 to 6, —C(O)—NH—C(CH$_3$)$_2$— and —C(O)—NH—CH(CH$_2$CH$_3$)— iii) optionally further ionic or nonionogenic monomers.

The copolymers present in the compositions may contain the monomers from groups i) and ii) and optionally iii) in varying amounts, and it is possible to combine any of the representatives from group i) with any of the representatives from group ii) and any of the representatives from group iii). Particularly preferred polymers have certain structural units which are described below.

For example, preference is given to inventive compositions which are characterized in that they comprise one or more copolymers which contain structural units of the formula III

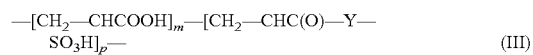
—[CH$_2$—CHCOOH]$_m$—[CH$_2$—CHC(O)—Y—SO$_3$H]$_p$—    (III)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—(CH$_2$)$_n$— where n=from 0 to 4, is —O—(C$_6$H$_4$)—, is —NH—C(CH$_3$)$_2$— or —NH—CH(CH$_2$CH$_3$)—.

These polymers are prepared by copolymerization of acrylic acid with an acrylic acid derivative containing sulfonic acid groups. Copolymerizing the acrylic acid derivative containing sulfonic acid groups with methacrylic acid leads to another polymer, the use of which in the inventive compositions is likewise preferred and which is characterized in that the compositions comprise one or more copolymers which contain structural units of the formula IV

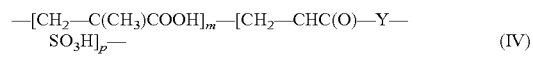
—[CH$_2$—C(CH$_3$)COOH]$_m$—[CH$_2$—CHC(O)—Y—SO$_3$H]$_p$—    (IV)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—(CH$_2$)$_n$— where n=from 0 to 4, is —O—(C$_6$H$_4$)—, is —NH—C(CH$_3$)$_2$— or —NH—CH(CH$_2$CH$_3$)—.

Acrylic acid and/or methacrylic acid can also be copolymerized entirely analogously with methacrylic acid derivatives containing sulfonic acid groups, which changes the structural units within the molecule. Thus, inventive compositions which comprise one or more copolymers which contain structural units of the formula V

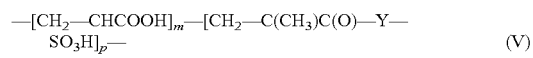
—[CH$_2$—CHCOOH]$_m$—[CH$_2$—C(CH$_3$)C(O)—Y—SO$_3$H]$_p$—    (V)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—(CH$_2$)$_n$— where n=from 0 to 4, is —O—(C$_6$H$_4$)—, is —NH—C(CH$_3$)$_2$— or —NH—CH(CH$_2$CH$_3$)— are likewise a preferred embodiment of the present invention, just like compositions which are characterized in that they comprise one or more copolymers which contain structural units of the formula VI

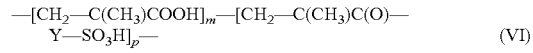
—[CH$_2$—C(CH$_3$)COOH]$_m$—[CH$_2$—C(CH$_3$)C(O)—Y—SO$_3$H]$_p$—    (VI)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—

$(CH_2)_n$— where n=from 0 to 4, is —O—$(C_6H_4)$—, is —NH—$C(CH_3)_2$— or —NH—$CH(CH_2CH_3)$—.

Instead of acrylic acid and/or methacrylic acid, or in addition thereto, it is also possible to use maleic acid as a particularly preferred monomer from group i). This leads to compositions preferred in accordance with the invention which are characterized in that they comprise one or more copolymers which contain structural units of the formula VII

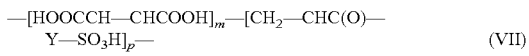

—[HOOCCH—CHCOOH]$_m$—[CH$_2$—CHC(O)—Y—SO$_3$H]$_p$— (VII)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—$(CH_2)_n$— where n=from 0 to 4, is —O—$(C_6H_4)$—, is —NH—$C(CH_3)_2$— or —NH—$CH(CH_2CH_3)$—, and to compositions which are characterized in that they comprise one or more copolymers which contain structural units of the formula VIII

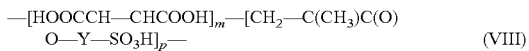

—[HOOCCH—CHCOOH]$_m$—[CH$_2$—C(CH$_3$)C(O)O—Y—SO$_3$H]$_p$— (VIII)

in which m and p are each a whole natural number between 1 and 2000, and Y is a spacer group which is selected from substituted or unsubstituted, aliphatic, aromatic or araliphatic hydrocarbon radicals having from 1 to 24 carbon atoms, preference being given to spacer groups in which Y is —O—$(CH_2)_n$— where n=from 0 to 4, is —O—$(C_6H_4)$—, is —NH—$C(CH_3)_2$— or —NH—$CH(CH_2CH_3)$—.

In summary, preference is given to machine dishwashing detergents according to the invention which comprise, as ingredient b), one or more copolymers which contain structural units of the formulae III and/or IV and/or V and/or VI and/or VII and/or VIII

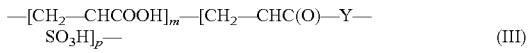

—[CH$_2$—CHCOOH]$_m$—[CH$_2$—CHC(O)—Y—SO$_3$H]$_p$— (III)

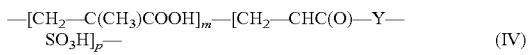

—[CH$_2$—C(CH$_3$)COOH]$_m$—[CH$_2$—CHC(O)—Y—SO$_3$H]$_p$— (IV)

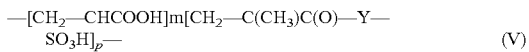

—[CH$_2$—CHCOOH]m[CH$_2$—C(CH$_3$)C(O)—Y—SO$_3$H]$_p$— (V)

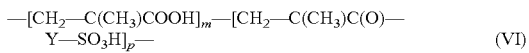

—[CH$_2$—C(CH$_3$)COOH]$_m$—[CH$_2$—C(CH$_3$)C(O)—Y—SO$_3$H]$_p$— (VI)

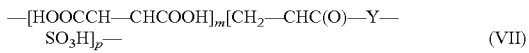

—[HOOCCH—CHCOOH]$_m$[CH$_2$—CHC(O)—Y—SO$_3$H]$_p$— (VII)

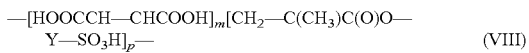

—[HOOCCH—CHCOOH]$_m$[CH$_2$—C(CH$_3$)C(O)O—Y—SO$_3$H]$_p$— (VIII)

in which m and p are each a whole natural number between 1 and 2000, and Y is a spacer group which is selected from substituted or unsubstituted aliphatic, aromatic or araliphatic hydrocarbon radicals having from 1 to 24 carbon atoms, preference being given to spacer groups in which Y is —O—$(CH_2)_n$— where n=0 to 4, is —O—$(C_6H_4)$—, is —NH—$C(CH_3)_2$— or —NH—$CH(CH_2CH_3)$—.

In the polymers, some or all of the sulfonic acid groups may be in neutralized form, i.e. the acidic hydrogen atom of the sulfonic acid group may be replaced in some or all of the sulfonic acid groups by metal ions, preferably alkali metal ions and in particular by sodium ions. Corresponding compositions which are characterized in that the sulfonic acid groups within the copolymer are present in partially or completely neutralized form are preferred in accordance with the invention.

The monomer distribution of the copolymers used in the inventive compositions is, in the case of copolymers which contain only monomers from groups i) and ii), preferably in each case from 5 to 95% by weight of i) or ii), more preferably from 50 to 90% by weight of monomer from group i) and from 10 to 50% by weight of monomer from group ii), based in each case on the polymer.

In the case of terpolymers, particular preference is given to those which contain from 20 to 85% by weight of monomer from group i), from 10 to 60% by weight of monomer from group ii), and from 5 to 30% by weight of monomer from group iii).

The molar mass of the polymers used in the inventive compositions can be varied in order to adapt the properties of the polymers to the desired intended use. Preferred machine dishwasher detergents are characterized in that the copolymers have molar masses of from 2000 to 200 000 gmol$^{-1}$, preferably from 4000 to 25 000 gmol$^{-1}$ and in particular from 5000 to 15 000 gmol$^{-1}$.

The content of one or more copolymers in the inventive compositions can vary depending on the intended use and desired product performance, and preferred inventive machine dishwashing detergents are characterized in that they contain the copolymer(s) in amounts of from 0.25 to 50% by weight, preferably from 0.5 to 35% by weight, more preferably from 0.75 to 20% by weight and in particular from 1 to 15% by weight.

As already mentioned above, particular preference is given to using in the inventive compositions both polyacrylates and the above-described copolymers of unsaturated carboxylic acids, monomers containing sulfonic acid groups and optionally further ionic or nonionogenic monomers. The polyacrylates have already been described in detail above. Particular preference is given to combinations of the above-described copolymers containing sulfonic acid groups with polyacrylates of low molar mass, for example in the range between 1000 and 4000 daltons. Such polyacrylates are commercially available under the trade names Sokalan® PA15 and Sokalan® PA25 (BASF).

Also suitable are copolymeric polycarboxylates, especially those of acrylic acid with methacrylic acid and of acrylic acid or methacrylic acid with maleic acid. Particularly suitable copolymers have been found to be those of acrylic acid with maleic acid which contain from 50 to 90% by weight of acrylic acid and from 50 to 10% by weight of maleic acid. Their relative molecular mass, based on free acids, is generally from 2000 to 100 000 g/mol, preferably from 20 000 to 90 000 g/mol and in particular from 30 000 to 80 000 g/mol.

The (co)polymeric polycarboxylates may be used either in the form of powder or in the form of an aqueous solution. The content in the compositions of (co)polymeric polycarboxylates is preferably from 0.5 to 20% by weight, in particular from 3 to 10% by weight.

To improve the water solubility, the polymers may also contain allylsulfonic acids, for example allyloxybenzenesulfonic acid and methallylsulfonic acid, as monomers.

Special preference is also given to biodegradable polymers composed of more than two different monomer units, for example those which contain, as monomers, salts of acrylic acid and of maleic acid and vinyl alcohol or vinyl alcohol derivatives, or which contain, as monomers, salts of acrylic acid and of 2-alkylallylsulfonic acid and sugar derivatives.

Further preferred copolymers have, as monomers, preferably acrolein and acrylic acid/acrylic acid salts or acrolein and vinyl acetate.

As further preferred builder substances, mention should equally be made of polymeric aminodicarboxylic acids, salts thereof or precursor substances thereof. Particular preference is given to polyaspartic acids and the salts and derivatives thereof.

Further suitable builder substances are polyacetals which can be obtained by reacting dialdehydes with polyolcarboxylic acids which have from 5 to 7 carbon atoms and at least 3 hydroxyl groups. Preferred polyacetals are obtained from dialdehydes such as glyoxal, glutaraldehyde, terephthalaldehyde, and mixtures thereof, and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary, for example acid-catalyzed or enzyme-catalyzed, processes. The hydrolysis products preferably have average molar masses in the range from 400 to 500 000 g/mol. Preference is given to a polysaccharide having a dextrose equivalent (DE) in the range from 0.5 to 40, in particular from 2 to 30, where DE is a common measure of the reducing action of a polysaccharide compared to dextrose, which has a DE of 100. It is also possible to use maltodextrins with a DE between 3 and 20 and dry glucose syrups with a DE between 20 and 37, and also yellow dextrins and white dextrins having relatively high molar masses in the range from 2000 to 30 000 g/mol.

The oxidized derivatives of such dextrins are their reaction, products with oxidizing agents which are capable of oxidizing at least one alcohol function of the saccharide ring to the carboxylic acid function. A product oxidized on $C_6$ of the saccharide ring may be particularly advantageous.

Oxydisuccinates and other derivatives of disuccinates, preferably ethylenediaminedisuccinate, are also further suitable cobuilders. In this case, ethylenediamine N,N'-disuccinate (EDDS) is preferably used in the form of its sodium or magnesium salts. In this connection, preference is also given to glycerol disuccinates and glycerol trisuccinates. Suitable use amounts in zeolite-containing and/or silicate-containing formulations are from 3 to 15% by weight.

Further organic cobuilders which can be used are, for example, acetylated hydroxycarboxylic acids or salts thereof, which may also be present in lactone form and which contain at least 4 carbon atoms and at least one hydroxyl group and a maximum of two acid groups.

A further class of substances having cobuilder properties is that of the phosphonates. These are in particular hydroxyalkane- and aminoalkanephosphonates. Among the hydroxyalkanephosphonates, 1-hydroxyethane-1,1-diphosphonate (HEDP) is of particular importance as cobuilder. It is preferably used in the form of the sodium salt, the disodium salt giving a neutral reaction and the tetrasodium salt an alkaline reaction (pH 9). Useful aminoalkanephosphbnates are preferably ethylenediaminetetramethylenephosphonate (EDTMP), diethylenetriaminepentamethylenephosphonate (DTPMP) and higher homologs thereof. They are preferably used in the form of the neutrally reacting sodium salts, for example as the hexasodium salt of EDTMP or as the hepta- and octasodium salt of DTPMP. From the class of the phosphonates, preference is given to using HEDP as builder. In addition, the aminoalkanephosphonates have a marked heavy metal-binding capacity. Accordingly, especially when the agents also comprise bleaches, it may be preferable to use aminoalkanephosphonates, especially DTPMP, or mixtures of the phosphonates mentioned.

In addition, it is possible to use all compounds which are capable of forming complexes with alkaline earth metal ions as cobuilders.

In the context of the present application, preferred compositions comprise one or more surfactant(s) from the groups of the anionic, nonionic, cationic and/or amphoteric surfactants.

The anionic surfactants used in acid form are preferably one or more substances from the group of the carboxylic acids, the sulfuric monoesters and the sulfonic acids, preferably from the group of the fatty acids, the fatty alkylsulfuric acids and the alkylarylsulfonic acids. In order to have sufficient surface-active properties, the compounds mentioned should have relatively long-chain hydrocarbon radicals, i.e. have at least 6 carbon atoms in the alkyl or alkenyl radical. Typically, the carbon chain distributions of the anionic surfactants are in the range from 6 to 40, preferably from 8 to 30 and in particular from 12 to 22 carbon atoms.

Carboxylic acids which find use as soaps in detergents in the form of their alkali metal salts are obtained industrially for the most part from native fats and oils by hydrolysis. While the alkaline hydrolysis which was carried out even in the nineteenth century led directly to the alkali metal salts (soaps), the practice today is to use only water for hydrolysis on the industrial scale, which hydrolyzes the fats into glycerol and the free acids. Processes employed on the industrial scale are, for example, hydrolysis in an autoclave or continuous high-pressure hydrolysis. In the context of the present invention, carboxylic acids which can be used in acid form as anionic surfactants are, for example, hexanoic acid (caproic acid), heptanoic acid (enanthic acid), octanoic acid (caprylic acid), nonanoic acid (pelargonic acid), decanoic acid (capric acid), undecanoic acid, etc. Preference is given in the context of the present invention to the use of fatty acids such as dodecanoic acid (lauric acid), tetradecanoic acid (myristic acid), hexadecanoic acid (palmitic acid), octadecanoic acid (stearic acid), eicosanoic acid (arachic acid), docosanoic acid (behenic acid), tetracosanoic acid (lignoceric acid), hexacosanoic acid (cerotic acid), triacotanoic acid (melissic acid), and also the unsaturated species 9c-hexadecenoic acid (palmitoleic acid), 6c-octadecenoic acid (petroselic acid), 6t-octadecenoic acid (petroselaidic acid), 9c-octadecenoic acid (oleic acid), 9t-octadecenoic acid (elaidic acid), 9c,12c-octadecadienoic acid (linoleic acid), 9t,12t-octadecadienoic acid (linolaidic acid) and 9c,12c,15c-octadecatrienoic acid (linolenic acid). For reasons of cost, preference is given not to using the pure species, but rather technical mixtures of the individual acids, as obtainable from fat hydrolysis. Such mixtures are, for example, coconut oil fatty acid (approx. 6% by weight of $C_8$, 6% by weight of $C_{10}$, 48% by weight of $C_{12}$, 18% by weight of $C_{14}$, 10% by weight of $C_{16}$, 2% by weight of $C_{18}$, 8% by weight of $C_{18'}$, 1% by weight of $C_{18''}$), palm kernel oil fatty acid (approx. 4% by weight of $C_8$, 5% by weight of $C_{10}$, 50% by weight of $C_{12}$, 15% by weight of $C_{14}$, 7% by weight of $C_{16}$, 2% by weight of $C_{18}$, 15% by weight of $C_{18'}$, 1% by weight of $C_{18''}$), tallow fatty acid (approx. 3% by weight of $C_{14}$, 26% by weight of $C_{16}$, 2% by weight of $C_{16'}$, 2% by weight of $C_{17}$, 17% by weight of $C_{18}$, 44% by weight of $C_{18'}$, 3% by weight of $C_{18''}$, 1% by weight of $C_{18'''}$), hardened tallow fatty acid (approx. 2% by weight of $C_{14}$, 28% by weight of $C_{16}$, 2% by weight of $C_{17}$, 63% by weight of $C_{18}$, 1% by weight of $C_{18'}$), technical oleic acid (approx. 1% by weight of $C_{12}$, 3% by weight of $C_{14}$, 5% by weight of $C_{16}$, 6% by weight of $C_{16'}$, 1% by weight of $C_{17}$, 2% by weight of $C_{18}$, 70% by weight of $C_{18'}$, 10% by weight of $C_{18''}$, 0.5% by weight of $C_{18'''}$), technical palmitic/stearic acid (approx. 1% by weight of $C_{12}$, 2% by weight of $C_{14}$, 45% by weight of $C_{16}$, 2% by weight of $C_{17}$, 47% by weight of $C_{18}$, 1% by weight of $C_{18'}$) and soybean oil fatty acid (approx. 2% by weight of $C_{14}$, 15% by weight of $C_{16}$, 5% by weight of $C_{18}$, 25% by weight of $C_{18'}$, 45% by weight of $C_{18''}$, 7% by weight of $C_{18'''}$).

Sulfuric monoesters of relatively long-chain alcohols are likewise anionic surfactants in their acid form and can be used in the context of the present invention. Their alkali metal salts, especially sodium salts, the fatty alcohol sulfates, are obtainable on the industrial scale from fatty alcohols which are reacted with sulfuric acid, chlorosulfonic acid, amidosulfonic alcohols or sulfur trioxide to give the alkylsulfuric acids in question and subsequently neutralized. The fatty alcohols are obtained from the fatty acids or fatty acid mixtures in question by high-pressure hydrogenation of the fatty acid methyl esters. The quantitatively most significant industrial process for the preparation of fatty alkyl sulfuric acids is the sulfonation of the alcohols with $SO_3$/air mixtures in special battery, falling-film or tube bundle reactors.

A further class of anionic surfactant acids which can be used in accordance with the invention is that of the alkyl ether sulfuric acids whose salts, the alkyl ether sulfates, feature higher water solubility and lower sensitivity toward water hardness (solubility of the calcium salts) in comparison to the alkyl sulfates. Like the alkyl sulfuric acids, alkyl ether sulfuric acids are synthesized from fatty alcohols which are reacted with ethylene oxide to give the fatty alcohol ethoxylates in question. Instead of ethylene oxide, it is also possible to use propylene oxide. The subsequent sulfonation with gaseous sulfur trioxide in short-path sulfonation reactors affords yields of above 98% of the alkyl ether sulfuric acids in question.

In the context of the present invention, it is also possible to use alkanesulfonic acids and olefinsulfonic acids as anionic surfactants in acid form. Alkanesulfonic acids may contain the sulfonic acid group in terminally bonded form (primary alkanesulfonic acids) or along the carbon chain (secondary alkanesulfonic acids), but only the secondary alkanesulfonic acids are of commercial significance. They are prepared by sulfochlorination or sulfoxidation of linear hydrocarbons. In the Reed sulfochlorination, n-paraffins are reacted with sulfur dioxide and chlorine with irradiation with UV light to give the corresponding sulfochlorides which on hydrolysis with alkalis directly afford the alkanesulfonates, on reaction with water the alkanesulfonic acids. Since di- and polysulfochlorides and also chlorinated hydrocarbons can occur as by-products of the free-radical reaction in the course of the sulfochlorination, the reaction is typically carried out only up to degrees of conversion of 30% and then terminated.

Another process for the preparation of alkanesulfonic acids is sulfoxidation, in which n-paraffins are reacted with sulfur dioxide and oxygen under irradiation with UV light. In this free-radical reaction, alkylsulfonyl radicals are formed gradually and react further with oxygen to give the alkylpersulfonyl radicals. The reaction with unconverted paraffin affords an alkyl radical and the alkylpersulfonic acid which decomposes into an alkylperoxysulfonyl radical and a hydroxyl radical. The reaction of the two radicals with unconverted paraffin affords the alkylsulfonic acids or water which reacts with alkylpersulfonic acid and sulfur dioxide to give sulfuric acid. In order to keep the yield of the two end products, alkylsulfonic acid and sulfuric acid, very high and to suppress side reactions, this reaction is typically only carried out up to degrees of conversion of 1% and then terminated.

Olefinsulfonates are prepared industrially by the reaction of α-olefins with sulfur trioxide. This forms zwitterions as an intermediate, which cyclize to give sultones. Under suitable conditions (alkaline or acidic hydrolysis), these sulfones react to give hydroxyalkanesulfonic acids or alkenesulfonic acids, both of which may likewise be used as anionic surfactant acids.

Alkylbenzenesulfonates as high-performance anionic surfactants have been known since the 1930s. At that time, monochlorination of "kogasin" fractions and subsequent Friedel-Crafts alkylation were used to prepare alkylbenzenes which were sulfonated with oleum and neutralized with sodium hydroxide solution. At the start of the 1950s, alkylbenzenesulfonates were prepared by tetramerizing propylene to give branched α-dodecylene, and the product was converted by a Friedel-Crafts reaction using aluminum trichloride or hydrogen fluoride to tetrapropylenebenzene which was subsequently sulfonated and neutralized. This economic means of preparing tetrapropylenebenzenesulfonates (Tps) led to the breakthrough for this class of surfactant, which subsequently replaced soaps as the main surfactant in detergents.

Owing to the inadequate biodegradability of Tps, there is a need to provide novel alkylbenzenesulfonates which are characterized by improved ecological performance. These requirements are satisfied by linear alkylbenzenesulfonates, which are nowadays almost the only alkylbenzenesulfonates prepared and are denoted by the abbreviation ABS or LAS.

Linear alkylbenzenesulfonates are prepared from linear alkylbenzenes which in turn are obtainable from linear olefins. For this purpose, petroleum fractions are separated on the industrial scale into the n-paraffins of the desired purity using molecular sieves and dehydrogenated to give the n-olefins, resulting in both α- and isoolefins. The resulting olefins are then reacted in the presence of acidic catalysts with benzene to give the alkylbenzenes, the selection of the Friedel-Crafts catalyst having an influence on the isomer distribution of the resulting linear alkylbenzenes: when aluminum trichloride is used, the content of the 2-phenyl isomers in the mixture with the 3-, 4-, 5- and other isomers is approx. 30% by weight; if, on the other hand, the catalyst used is hydrogen fluoride, the content of 2-phenyl isomer can be lowered to approx. 20% by weight. Finally, the linear alkylbenzenes are nowadays sulfonated on the industrial scale with oleum, sulfuric acid or gaseous sulfur trioxide, of which the latter is by far the most significant. For the sulfonation, special film or tube-bundle reactors are used and afford, as the product, 97% by weight alkylbenzenesulfonic acid (ABSA), which can be used as the anionic surfactant acid in the context of the present invention.

The selection of the neutralizing agent makes it possible to obtain a very wide variety of salts, i.e. alkylbenzenesulfonates, from the ABSAs. For economic reasons, preference is given to preparing and using the alkali metal salts and, among these, preferably the sodium salts of ABSA. These can be described by the general formula IX:

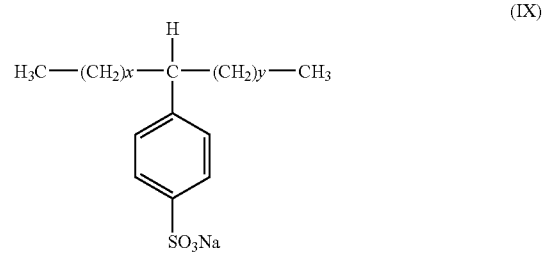

in which the sum of x and y is typically between 5 and 13. Anionic surfactants in acid form which are preferred in accordance with the invention are $C_{8-16}$-alkylbenzene sulfonic acids, preferably $C_{9-13}$-alkylbenzenesulfonic acids. In the context of the present invention, preference is also given to using $C_{8-16}$-alkylbenzene sulfonic acids, preferably $C_{9-13}$-alkylbenzenesulfonic acids which derive from alkylbenzenes which have a tetralin content below 5% by weight, based on the alkylbenzene. Preference is further given to using alkylbenzenesulfonic acids whose alkylbenzenes have been prepared by the HF process, so that the $C_{8-16}$-alkylbenzenesulfonic acids, preferably $C_{9-13}$-alkylbenzenesulfonic acids used have a content of 2-phenyl isomer below 22% by weight, based on the alkylbenzenesulfonic acid.

The aforementioned anionic surfactants in their acid form may be used alone or in a mixture with one another. However, it is also possible and preferred that further, preferably acidic, ingredients of detergents be added in amounts of from 0.1 to 40% by weight, preferably from 1 to 15% by weight and in particular from 2 to 10% by weight, based in each case on the weight of the mixture to be converted, to the anionic surfactant in acid form before it is added to the carrier material(s).

It will be appreciated that it is also possible to use the anionic surfactants in semineutralized or fully neutralized form. In that case, these salts may be present as a solution, suspension or emulsion in the granulation liquid but may also be part of the fixed bed as a solid. Possible cations for such anionic surfactants are, in addition to the alkali metals (here in particular sodium and potassium salts), ammonium and mono-, di- or triethanolalkonium ions. Instead of mono-, di- or triethanolamine, it is also possible for the analogous representatives of mono-, di- or trimethanolamine or those of the alkanolamines of higher alcohols to be quaternized and to be present as the cation.

It is advantageously also possible to use cationic surfactants as the active substance. The cationic surfactant may be added directly into the mixer in its supply form, or be sprayed onto the solid support in the form of a liquid to pasty cationic surfactant formulation form. Such cationic surfactant formulation forms can be prepared, for example, by mixing commercial cationic surfactants with assistants such as nonionic surfactants, polyethylene glycols or polyols. It is also possible to use lower alcohols such as ethanol and isopropanol, in which case the amount of such lower alcohols in the liquid cationic surfactant preparation form should, for the above-mentioned reasons, be below 10% by weight.

Useful cationic surfactants for the inventive compositions include all customary substances, and there is a distinct preference for cationic surfactants having textile-softening action.

The inventive compositions may comprise, as cationic active substances having textile-softening action, one or more cationic textile-softening agents of the formulae X, XI or XII:

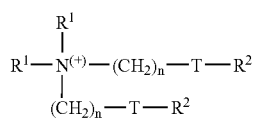

(X)

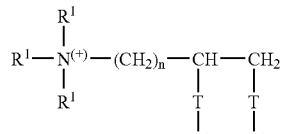

(XI)

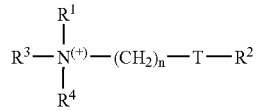

(XII)

where each $R^1$ group is independently selected from $C_{1-6}$-alkyl, -alkenyl or -hydroxyalkyl groups; each $R^2$ group is independently selected from $C_{8-28}$-alkyl or -alkenyl groups; $R^3=R^1$ or $(CH_2)_n$-T-$R^2$; $R^4=R^1$ or $R^2$ or $(CH_2)_n$-T-$R^2$; T=—$CH_2$—, —O—CO— or —CO—O— and n is an integer from 0 to 5.

In preferred embodiments of the present invention, the compositions additionally comprise nonionic surfactant(s) as the active substance.

The nonionic surfactants used are preferably alkoxylated, advantageously ethoxylated, in particular primary alcohols having preferably from 8 to 18 carbon atoms and on average from 1 to 12 mol of ethylene oxide (EO) per mole of alcohol in which the alcohol radical may be linear or preferably 2-methyl-branched, or may contain a mixture of linear and methyl-branched radicals, as are typically present in oxo alcohol radicals. However, especially preferred alcohol ethoxylates have linear radicals of alcohols of natural origin having from 12 to 18 carbon atoms, for example of coconut, palm, tallow fat or oleyl alcohol, and on average from 2 to 8 EO per mole of alcohol. The preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO or 7 EO and mixtures thereof, such as mixtures of $C_{12-14}$-alcohol having 3 EO and $C_{12-18}$-alcohol having 5 EO. The degrees of ethoxylation specified are statistical average values which may be an integer or a fraction for a specific product. Preferred alcohol ethoxylates have a narrowed homolog distribution (narrow range ethoxylates, NRE). In addition to these nonionic surfactants, it is also possible to use fatty alcohols having more than 12 EO. Examples thereof are tallow fatty alcohol having 14 EO, 25 EO, 30 EO or 40 EO.

In addition, further nonionic surfactants which may be used are also alkyl glycosides of the general formula $RO(G)_x$ in which R is a primary straight-chain or methyl-branched, in particular 2-methyl-branched, aliphatic radical having from 8 to 22, preferably from 12 to 18, carbon atoms and G is the symbol which is a glycose unit having 5 or 6 carbon atoms, preferably glucose. The degree of oligomerization x, which specifies the distribution of monoglycosides and oligoglycosides, is any number between 1 and 10; x is preferably from 1.2 to 1.4.

A further class of nonionic surfactants used with preference, which are used either as the sole nonionic surfactant or in combination with other nonionic surfactants, are alkoxylated, preferably ethoxylated or ethoxylated and propoxylated, fatty acid alkyl esters, preferably having from 1 to 4 carbon atoms in the alkyl chain, in particular fatty acid methyl esters.

Nonionic surfactants of the amine oxide type, for example N-cocoalkyl-N,N-dimethylamine oxide and N-tallow alkyl-N,N-hydroxyethylamine oxide, and of the fatty acid alkanolamide type may also be suitable. The amount of these nonionic surfactants is preferably not more than that of the ethoxylated fatty alcohols, in particular not more than half thereof.

Further suitable surfactants are polyhydroxy fatty acid amides of the formula XIII

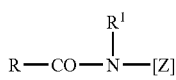
(XIII)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can typically be obtained by reductively aminating a reducing sugar with ammonia, an alkylamine or an alkanolamine, and subsequently acylating with a fatty acid, a fatty acid alkyl ester or a fatty acid chloride.

The group of polyhydroxy fatty acid amides also includes compounds of the formula XIV

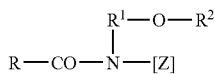
(XIV)

in which R is a linear or branched alkyl or alkenyl radical having from 7 to 12 carbon atoms, $R^1$ is a linear, branched or cyclic alkyl radical or an aryl radical having from 2 to 8 carbon atoms and $R^2$ is a linear, branched or cyclic alkyl radical or an aryl radical or an oxyalkyl radical having from 1 to 8 carbon atoms, preference being given to $C_{1-4}$-alkyl or phenyl radicals, and [Z] is a linear polyhydroxyalkyl radical whose alkyl chain is substituted by at least two hydroxyl groups, or alkoxylated, preferably ethoxylated or propoxylated, derivatives of this radical.

[Z] is preferably obtained by reductive amination of a reduced sugar, for example glucose, fructose, maltose, lactose, galactose, mannose or xylose. The N-alkoxy- or N-aryloxy-substituted compounds can be converted to the desired polyhydroxy fatty acid amides by reaction with fatty acid methyl esters in the presence of an alkoxide as catalyst.

It is particularly preferred for many applications when the ratio of anionic surfactant(s) to nonionic surfactant(s) is between 10:1 and 1:10, preferably between 7.5:1 and 1:5 and in particular between 5:1 and 1:2. Preference is given to inventive containers which contain surfactant(s), preferably anionic and/or nonionic surfactant(s), in amounts of from 5 to 80% by weight, preferably of from 7.5 to 70% by weight, more preferably of from 10 to 60% by weight and in particular of from 12.5 to 50% by weight, based in each case on the weight of the enclosed solids.

As already mentioned, the use of surfactants in detergents for machine dishwashing is preferably restricted to the use of nonionic surfactants in small amounts. Inventive compositions for machine dishwashing therefore preferably comprise only certain nonionic surfactants, which are described below.

The surfactants used in machine dishwasher detergents are typically only low-foaming nonionic surfactants. Representatives from the group of the anionic, cationic or amphoteric surfactants are therefore of lesser importance. The nonionic surfactants used are preferably alkoxylated, advantageously ethoxylated, in particular primary alcohols having preferably from 8 to 18 carbon atoms and on average from 1 to 12 mol of ethylene oxide (EO) per mole of alcohol in which the alcohol radical may be linear or preferably 2-methyl-branched, or may contain a mixture of linear and methyl-branched radicals, as are typically present in oxo alcohol radicals. However, especially preferred alcohol ethoxylates have linear radicals of alcohols of natural origin having from 12 to 18 carbon atoms, for example of coconut, palm, tallow fat or oleyl alcohol, and on average from 2 to 8 EO per mole of alcohol. The preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO or 7 EO and mixtures thereof, such as mixtures of $C_{12-14}$-alcohol having 3 EO and $C_{12-18}$-alcohol having 5 EO. The degrees of ethoxylation specified are statistical average values which may be an integer or a fraction for a specific product. Preferred alcohol ethoxylates have a narrowed homolog distribution (narrow range ethoxylates, NRE). In addition to these nonionic surfactants, it is also possible to use fatty alcohols having more than 12 EO. Examples thereof are tallow fatty alcohol having 14 EO, 25 EO, 30 EO or 40 EO.

Especially in the case of detergents for machine dishwashing, it is preferred that they comprise a nonionic surfactant which has a melting point above room temperature, preferably a nonionic surfactant having a melting point above 20° C. Nonionic surfactants to be used with preference have melting points above 25° C.; nonionic surfactants to be used with particular preference have melting points between 25 and 60° C., in particular between 26.6 and 43.3° C.

Suitable nonionic surfactants which have melting or softening points in the temperature range specified are, for example, low-foaming nonionic surfactants which may be solid or highly viscous at room temperature. When nonionic surfactants which have a high viscosity at room temperature are used, they preferably have a viscosity above 20 Pas, more preferably above 35 Pas and in particular above 40 Pas. Nonionic surfactants which have a waxlike consistency at room temperature are also preferred.

Nonionic surfactants which are solid at room temperature and are to be used with preference stem from the group of alkoxylated nonionic surfactants, in particular the ethoxylated primary alcohols and mixtures of these surfactants with structurally complex surfactants, such as polyoxypropylene/polyoxyethylene/polyoxypropylene (PO/EO/PO) surfactants. Such (PO/EO/PO) nonionic surfactants are additionally notable for good foam control.

In a preferred embodiment of the present invention, the nonionic surfactant with a melting point above room temperature is an ethoxylated nonionic surfactant which has resulted from the reaction of a monohydroxyalkanol or alkylphenol having from 6 to 20 carbon atoms with preferably at least 12 mol, more preferably at least 15 mol, in particular at least 20 mol, of ethylene oxide per mole of alcohol or alkylphenol.

A nonionic surfactant which is solid at room temperature and is to be used with particular preference is obtained from a straight-chain fatty alcohol having from 16 to 20 carbon atoms ($C_{16-20}$-alcohol), preferably a $C_{18}$-alcohol, and at least 12 mol, preferably at least 15 mol and in particular at least 20 mol, of ethylene oxide. Of these, the "narrow range ethoxylates" (see above) are particularly preferred.

The nonionic surfactant which is solid at room temperature preferably additionally has propylene oxide units in the molecule. Such PO units make up preferably up to 25% by weight, more preferably up to 20% by weight and in particular up to 15% by weight, of the total molar mass of the nonionic surfactant. Particularly preferred nonionic surfactants are ethoxylated monohydroxyalkanols or alkylphenols which additionally have polyoxyethylene-polyoxypropylene block copolymer units. The alcohol or alkylphenol moiety of such nonionic surfactant molecules preferably makes up more than 30% by weight, more preferably more than 50% by weight and in particular more than 70% by weight, of the total molar mass of such nonionic surfactants.

Further nonionic surfactants which have melting points above room temperature and are to be used with particular preference contain from 40 to 70% of a polyoxypropylene/polyoxyethylene/polyoxypropylene block polymer blend which contains 75% by weight of an inverse block copolymer of polyoxyethylene and polyoxypropylene having 17 mol of ethylene oxide and 44 mol of propylene oxide, and 25% by weight of a block copolymer of polyoxyethylene and polyoxypropylene initiated with trimethylolpropane and containing 24 mol of ethylene oxide and 99 mol of propylene oxide per mole of trimethylolpropane.

Nonionic surfactants which can be used with particular preference are obtainable, for example, under the name Poly Tergent® SLF-18 from Olin Chemicals.

A further preferred surfactant can be described by the formula $$R^1O[CH_2CH(CH_3)O]_x[CH_2CH_2O]_y[CH_2CH(OH)R^2]$$

in which $R^1$ is a linear or branched aliphatic hydrocarbon radical having from 4 to 18 carbon atoms or mixtures thereof, $R^2$ is a linear or branched hydrocarbon radical having from 2 to 26 carbon atoms or mixtures thereof, and x is a value between 0.5 and 1.5, and y is a value of at least 15.

Further nonionic surfactants which can be used with preference are the end group-capped poly(oxyalkylated) nonionic surfactants of the formula $$R^1O[CH_2CH(R^3)O]_x[CH_2]_kCH(OH)[CH_2]_jOR^2$$

in which $R^1$ and $R^2$ are linear or branched, saturated or unsaturated, aliphatic or aromatic hydrocarbon radicals having from 1 to 30 carbon atoms, $R^3$ is H or a methyl, ethyl, n-propyl, isopropyl, n-butyl, 2-butyl or 2-methyl-2-butyl radical, x is a value between 1 and 30, k and j are values between 1 and 12, preferably between 1 and 5. When the value x is $\geq 2$, each $R^3$ in the above formula may be different. $R^1$ and $R^2$ are preferably linear or branched, saturated or unsaturated, aliphatic or aromatic hydrocarbon radicals having from 6 to 22 carbon atoms, particular preference being given to radicals having from 8 to 18 carbon atoms. For the $R^3$ radical, particular preference is given to H, —$CH_3$ or —$CH_2CH_3$. Particularly preferred values for x are in the range from 1 to 20, in particular from 6 to 15.

As described above, each $R^3$ in the above formula may be different if x is $\geq 2$. This allows the alkylene oxide unit in the square brackets to be varied. When x is, for example, 3, the $R^3$ radical may be selected so as to form ethylene oxide ($R^3$=H) or propylene oxide ($R^3$=$CH_3$) units which can be joined together in any sequence, for example (EO)(PO)(EO), (EO)(EO)(PO), (EO)(EO)(EO), (PO)(EO)(PO), (PO)(PO)(EO) and (PO)(PO)(PO). The value 3 for x is selected here by way of example and it is entirely possible for it to be larger, the scope of variation increasing with increasing x values and embracing, for example, a large number of (EO) groups combined with a small number of (PO) groups, or vice versa.

Especially preferred end group-capped poly(oxyalkylated) alcohols of the above formula have values of k=1 and j=1, so that the above formula is simplified to $$R^1O[CH_2CH(R^3)O]_xCH_2CH(OH)CH_2OR^2.$$

In the latter formula, $R^1$, $R^2$ and $R^3$ are each as defined above and x is a number from 1 to 30, preferably from 1 to 20 and in particular from 6 to 18. Particular preference is given to surfactants in which the $R^1$ and $R^2$ radicals have from 9 to 14 carbon atoms, $R^3$ is H and x assumes values of from 6 to 15.

To increase the washing or cleaning performance, inventive compositions may contain enzymes, in which case it is possible in principle to use any enzymes established for these purposes in the prior art. These include in particular proteases, amylases, lipases, hemicellulases, cellulases or oxidoreductases, and preferably mixtures thereof. These enzymes are in principle of natural origin; starting from the natural molecules, improved variants for use in detergents are available and are preferably used accordingly. Inventive compositions preferably contain enzymes in total amounts of from $1 \times 10^{-6}$ to 5 percent by weight based on active protein. The protein concentration may be determined with the aid of known methods, for example the BCA method (bicinchonic acid; 2,2'-biquinolyl-4,4'-dicarboxylic acid) or the biuret method.

Among the proteases, preference is given to those of the subtilisin type. Examples thereof include the subtilisins. BPN' and Carlsberg, protease PB92, the subtilisins 147 and 309, *Bacillus lentus* alkaline protease, subtilisin DY and the enzymes thermitase and proteinase K which can be classified to the subtilases but no longer to the subtilisins in the narrower sense, and the proteases TW3 and TW7. The subtilisin Carlsberg is available in a developed form under the trade name Alcalase® from Novozymes A/S, Bagsværd, Denmark. The subtilisins 147 and 309 are sold under the trade names Esperase® and Savinase® respectively by Novozymes. The variants listed under the name BLAP® are derived from the protease of *Bacillus lentus* DSM 5483.

Further examples of useful proteases are the enzymes available under the trade names Durazym®, Relase®, Everlase®, Nafizym, Natalase®, Kannase® and Ovozymes® from Novozymes, those under the trade names Purafect®, Purafect®OxP and Properase® from Genencor, that under the trade name Protosol® from Advanced Biochemicals Ltd., Thane, India, that under the trade name Wuxi® from Wuxi Snyder Bioproducts Ltd., China, those under the trade names Proleather® and Protease P® from Amano Pharmaceuticals Ltd., Nagoya, Japan and that under the name Proteinase K-16 from Kao Corp., Tokyo, Japan.

Examples of amylases which can be used in accordance with the invention are the α-amylases from *Bacillus licheniformis*, from *B. amyloliquefaciens* or from *B. stearothermophilus* and developments thereof which have been improved for use in detergents. The *B. licheniformis* enzyme is available from Novozymes under the name Termamyl® and from Genencor under the name Purastar®ST. Development products of this α-amylase are obtainable from Novozymes under the trade names Duramyl® and Termamyl®ultra, from Genencor under the name Purastar®OxAm and from Daiwa Seiko Inc., Tokyo, Japan as Keistase®. The *B. amyloliquefaciens* α-amylase is sold by Novozymes under the name BAN®, and variants derived from the *B. stearothermophilus* α-amylase under the names BSG® and Novamyl®, likewise from Novozymes.

Enzymes which should additionally be emphasized for this purpose are the α-amylase from *Bacillus* sp. A 7-7 (DSM 12368), and the cyclodextrin glucanotransferase (CGTase) from *B. agaradherens* (DSM 9948); it is equally possible to use fusion products of the molecules mentioned.

Also suitable are the developments of α-amylase from *Aspergillus niger* and *A. oryzae*, which are available under the trade names Fungamyl® from Novozymes. Another example of a commercial product is Amylase-LT®.

Inventive compositions may comprise lipases or cutinases, especially owing to their triglyceride-cleaving activities, but also in order to generate peracids in situ from suitable precursors. Examples thereof include the lipases which were originally obtainable from *Humicola lanuginosa* (*Thermomyces lanuginosus*) or have been developed, in particular those with the D96L amino acid substitution. They are sold, for example, under the trade names Lipolase®, Lipolase®Ultra, LipoPrime®, Lipozyme® and Lipex® by Novozymes. It is additionally possible, for example, to use the cutinases which have originally been isolated from *Fusarium solani pisi* and *Humicola insolens*. Lipases which are also useful can be obtained under the designations Lipase CE®, Lipase P®, Lipase B®, Lipase CES®, Lipase AKG®, *Bacillis* sp. Lipase®, Lipase AP®, Lipase M-AP® and Lipase AML® from Amano. Examples of lipases and cutinases from Genencor which can be used are those whose starting enzymes have originally been isolated from *pseudomonas mendocina* and *Fusarium solanii*. Other important commercial products include the M1 Lipase® and Lipomax® preparations originally sold by Gist-Brocades and the enzymes sold under the names Lipase MY-30®, Lipase OF® and Lipase PL® by Meito Sangyo KK, Japan, and also the product Lumafast® from Genehcor.

Inventive compositions may, especially when they are intended for the treatment of textiles, comprise cellulases, depending on the purpose either as pure enzymes, as enzyme preparations or in the form of mixtures in which the individual components advantageously complement one another with respect to their different performance aspects. These performance aspects include in particular contributions to the primary washing performance, to the secondary washing performance of the composition (antiredeposition action or graying inhibition) and hand (fabric action), up to exerting a "stone-wash" effect.

A useful fungal, endoglucanase(EG)-rich cellulase preparation and developments thereof are supplied under the trade name Celluzyme® from Novozymes. The products Endolase® and Carezyme®, likewise available from Novozymes, are based on the *H. insolens* DSM 1800 50 kD EG and 43 kD EG respectively. Further commercial products of this company, which may be used, are Cellusoft® and Renozyme®. It is equally possible to use the *Melanocarpus* 20 kD EG cellulase, which is available under the trade names Ecostone® and Biotouch® from AB Enzymes, Finland. Further commercial products from AB Enzymes are Econase® and Ecopulp®. A further suitable cellulase from *Bacillus* sp. CBS 670.93 is available under the trade name Puradex® from Genencor. Other commercial products from Genencor are Genencor detergent cellulase L and IndiAge®Neutra.

Inventive compositions may comprise further enzymes which are combined under the term hemicellulases. These include, for example, mannanases, xanthane lyases, pectin lyases (=pectinases), pectin esterases, pectate lyases, xyloglucanases (=xylanases), pullulanases and β-glucanases. Suitable mannanases are available, for example, under the names Gamanase® and Pektinex AR® from Novozymes, under the name Rohapec® B1L from AB Enzymes and under the name Pyrolase® from Diversa Corp., San Diego, Calif., USA. The β-glucanase obtained from *B. subtilis* is available under the name Cereflo® from Novozymes.

In order to enhance the bleaching action, inventive detergents may comprise oxidoreductases, for example oxidases, oxygenases, catalases, peroxidases, such as haloperoxidases, chloroperoxidases, bromoperoxidases, lignin peroxidases, glucose peroxidases or manganese peroxidases, dioxygenases or laccases (phenol oxidases, polyphenol oxidases). Suitable commercial products include Denilite® 1 and 2 from Novozymes. Advantageously, preferably organic, more preferably aromatic, compounds which interact with the enzymes are additionally added in order to enhance the activity of the oxidoreductases concerned (enhancers), or to ensure the electron flux in the event of large differences in the redox potentials of the oxidizing enzymes and the soilings (mediators).

The enzymes used in inventive compositions either stem originally from microorganisms, for example of the genera *Bacillus, Streptomyces, Humicola*, or *pseudomonas*, and/or are produced in biotechnology processes known per se by suitable microorganisms, for instance by transgenic expression hosts of the genera *Bacillus* or filamentous fungi.

The enzymes in question are favorably purified via processes which are established per se, for example via precipitation, sedimentation, concentration, filtration of the liquid phases, microfiltration, ultrafiltration, the action of chemicals, deodorization or suitable combinations of these steps.

The enzymes may be added to inventive compositions in any form established in the prior art. These include, for example, the solid preparations obtained by granulation, extrusion or lyophilization, or, especially in the case of liquid or gel-form compositions, solutions of the enzymes, advantageously highly concentrated, low in water and/or admixed with stabilizers.

Alternatively, the enzymes may be encapsulated either for the solid or for the liquid administration form, for example by spray-drying or extrusion of the enzyme solution together with a preferably natural polymer, or in the form of capsules, for example those in which the enzymes are enclosed as in a solidified gel, or in those of the core-shell type, in which an enzyme-containing core is coated with a water-, air- and/or chemical-impermeable protective layer. It is possible in layers applied thereto to additionally apply further active ingredients, for example stabilizers, emulsifiers, pigments, bleaches or dyes. Such capsules are applied by methods known per se, for example by agitated or roll granulation or in fluidized bed processes. Advantageously, such granules, for example as a result of application of polymeric film formers, are low-dusting and storage-stable owing to the coating.

It is also possible to formulate two or more enzymes together, so that a single granule has a plurality of enzyme activities.

A protein and/or enzyme present in an inventive composition may be protected, particularly during storage, from damage, for example inactivation, denaturation or decay, for instance by physical influences, oxidation or proteolytic cleavage. When the proteins and/or enzymes are obtained microbially, particular preference is given to inhibiting proteolysis, especially when the compositions also comprise proteases. For this purpose, inventive compositions may comprise stabilizers; the provision of such compositions constitutes a preferred embodiment of the present invention.

One group of stabilizers is that of reversible protease inhibitors. Frequently, benzamidine hydrochloride, borax, boric acids, boronic acids or salts or esters thereof are used, and of these in particular derivatives having aromatic groups, for example ortho-, meta- or para-substituted phenylboronic acids, or the salts or esters thereof. Peptide aldehydes, i.e. oligopeptides with reduced C-terminus are also suitable. Peptidic protease inhibitors which should be mentioned include ovomucoid and leupeptin; an additional option is the formation of fusion proteins of proteases and peptide inhibitors.

Further enzyme stabilizers are amino alcohols such as mono-, di-, triethanol- and -propanolamine and mixtures thereof, aliphatic carboxylic acids up to $C_{12}$, such as succinic acid, other dicarboxylic acids or salts of the acids mentioned. End group-capped fatty acid amide alkoxylates can also be used as stabilizers.

Lower aliphatic alcohols, but in particular polyols, for example glycerol, ethylene glycol, propylene glycol or sorbitol, are further frequently used enzyme stabilizers. Diglycerol phosphate also protects against denaturation by physical influences. Calcium salts are likewise used, for example calcium acetate or calcium formate, as are magnesium salts.

Polyamide oligomers or polymeric compounds such as lignin, water-soluble vinyl copolymers or cellulose ethers, acrylic polymers and/or polyamides stabilize the enzyme preparation against influences including physical influences or pH fluctuations. Polyamine N-oxide-containing polymers act simultaneously as enzyme stabilizers and as dye transfer inhibitors. Other polymeric stabilizers are the linear $C_8$-$C_{18}$ polyoxy-alkylenes. Alkylpolyglycosides can likewise stabilize the enzymatic components of the inventive composition and even increase their performance. Crosslinked N-containing compounds fulfill a double function as soil release agents and as enzyme stabilizers.

Reducing agents and antioxidants, such as sodium sulfite or reducing sugars, increase the stability of the enzymes against oxidative decay.

Preference is given to using combinations of stabilizers, for example of polyols, boric acid and/or borax, the combination of boric acid or borate, reducing salts and succinic acid or other dicarboxylic acids or the combination of boric acid or borate with polyols or polyamino compounds and with reducing salts. The action of peptide-aldehyde stabilizers can be increased by the combination with boric acid and/or boric acid derivatives and polyols, and further enhanced by the additional use of divalent cations, for example calcium ions.

Particular preference is given in the context of the present invention to the use of liquid enzyme formulations. Preference is given here to inventive compositions which additionally comprise enzymes and/or enzyme preparations, preferably solid and/or liquid protease preparations and/or amylase preparations, in amounts of from 1 to 5% by weight, preferably of from 1.5 to 4.5% by weight and in particular from 2 to 4% by weight, based in each case on the overall composition.

The electrolytes used from the group of the inorganic salts may be a wide range of highly varying salts. Preferred cations are the alkali metals and alkaline earth metals; preferred anions are the halides and sulfates. From a production point of view, preference is given to the use of NaCl or $MgCl_2$ in the inventive granules.

In order to bring the pH of solutions of the inventive compositions into the desired range, it may be appropriate to use pH modifiers. It is possible here to use all known acids or alkalis, as long as their use is not forbidden on performance or ecological grounds or on grounds of consumer protection. Typically, the amount of these modifiers does not exceed 1% by weight of the overall formulation.

Hydrotropes or solubilizers refer to substances which, by their presence, make other compounds which are virtually insoluble in a certain solvent soluble or emulsifiable in this solvent (solubilization). There are solubilizers which enter into a molecular bond with the sparingly soluble substance and those which act by micelle formation. It can also be said that solubilizers actually impart dissolution power to a "latent" solvent. In the case of water as the (latent) solvent, reference is made usually to hydrotropes instead of solubilizers, and in certain cases it is better to refer to emulsifiers.

Useful foam inhibitors which may be used in the inventive compositions include soaps, oils, fats, paraffins or silicone oils, which may optionally be applied to support materials. Suitable support materials are, for example, inorganic salts such as carbonates or sulfates, cellulose derivatives or silicates and mixtures of the aforementioned materials. Compositions which are preferred in the context of the present application comprise paraffins, preferably unbranched paraffins (n-paraffins) and/or silicones, preferably linear polymeric silicones which have the composition according to the scheme $(R_2SiO)x$ and are also referred to as silicone oils. These silicone oils are commonly clear, colorless, neutral, odorless, hydrophobic liquids having a molecular weight between 1000-150 000, and viscosities between 10 and 1 000 000 mPa·s.

Suitable antiredeposition agents, which are also referred to as soil repellents, are, for example, nonionic cellulose ethers, such as methylcellulose and methylhydroxypropylcellulose having a proportion of methoxy groups of from 15 to 30% by weight and of hydroxypropyl groups of from 1 to 15% by weight, based in each case on the nonionic cellulose ethers, and the prior art polymers of phthalic acid and/or terephthalic acid or derivatives thereof, in particular polymers of ethylene terephthalates and/or polyethylene glycol terephthalates or anionically and/or nonionically modified derivatives thereof. Of these, particular preference is given to the sulfonated derivatives of phthalic acid polymers and terephthalic acid polymers.

Optical brighteners (known as "whiteners") may be added to the inventive compositions in order to eliminate graying and yellowing of the treated textiles. These substances attach to the fibers and bring about brightening and simulated bleaching action by converting invisible ultraviolet radiation to visible longer-wavelength light, in the course of which the ultraviolet light absorbed from sunlight is radiated as pale bluish fluorescence and, together with the yellow shade of the grayed or yellowed laundry, results in pure white. Suitable compounds stem, for example, from the substance classes of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazole, benzisoxazole and benzimidazole systems, and the pyrene derivatives substituted by heterocycles.

Graying inhibitors have the task of keeping the soil detached from the fiber suspended in the liquor, thus preventing the soil from reattaching. Suitable for this purpose are water-soluble colloids, usually of organic nature, for example the water-soluble salts of polymeric carboxylic acids, size, gelatin, salts of ether sulfonic acids of starch or of cellulose, or salts of acidic sulfuric esters of cellulose or of starch. Water-soluble polyamides containing acidic groups are also suitable for this purpose. In addition, it is possible to use soluble starch preparations, and starch products other than those mentioned above, for example degraded starch, aldehyde starches, etc. It is also possible to use polyvinylpyrrolidone. Also usable as graying inhibitors are cellulose ethers such as carboxymethylcellulose (sodium salt), methylcellulose, hydroxyalkylcellulose and mixed ethers such as methylhydroxyethylcellulose, methylhydroxypropylcellulose, methylcarboxymethylcellulose and mixtures thereof.

Since textile fabrics, in particular those made of rayon, viscose, cotton and mixtures thereof, can tend to crease because the individual fibers are sensitive toward bending, folding, compressing and crushing transverse to the fiber direction, the inventive, compositions may comprise synthetic anticrease agents. These include, for example, synthetic products based on fatty acids, fatty acid esters, fatty acid amides, fatty acid alkylol esters, fatty acid alkylolamides or fatty alcohols, which have usually been reacted with ethylene oxide, or products based on lecithin or modified phosphoric esters. A substance suitable to a particular degree for textile finishing and care is cottonseed oil which can be produced, for example, by extractively pressing the brown cleaned cottonseeds and refining with about 10% sodium hydroxide or by extracting with hexane at 60-70° C. Such cotton oils contain from 40 to 55% by weight of linoleic acid, from 16 to 26% by weight of oleic acid and from 20 to 26% by weight of palmitic acid. Further particularly preferred products for fiber smoothing and fibercare are the glycerides, especially the monoglycerides of fatty acids, for example glycerol monooleate or glycerol monostearate.

To control microorganisms, the inventive compositions may comprise active antimicrobial ingredients. A distinction is drawn here, depending on the antimicrobial spectrum and mechanism of action, between bacteriostats and bactericides, fungistats and fungicides, etc. Important substances from these groups are, for example, benzalkonium chlorides, alkylarylsulfonates, halophenols and phenylmercuric acetate, although it is also possible to dispense entirely with these compounds in the inventive compositions.

In order to prevent undesired changes, caused by the action of oxygen and other oxidative processes, to the detergents and/or the textiles treated, the inventive compositions may comprise antioxidants. This class of compound includes, for example, substituted phenols, hydroquinones, pyrocatechols and aromatic amines, and also organic sulfides, polysulfides, dithiocarbamates, phosphites and phosphonates.

Increased wear comfort can result from the additional use of antistats which are additionally added to the inventive compositions. Antistats increase the surface conductivity and thus permit improved discharge of charges formed. External antistats are generally substances having at least one hydrophilic molecular ligand and impart to the surfaces a more or less hygroscopic film. These usually interface-active antistats can be subdivided into nitrogen antistats (amines, amides, quaternary ammonium compounds), phosphorus antistats (phosphoric esters) and sulfur antistats (alkylsulfonates, alkyl sulfates). Lauryldimethylbenzylammonium (or stearyldimethyl-benzylammonium) chlorides are likewise suitable as antistats for textiles or as additives for detergents, in which case a hand effect is additionally achieved.

Repellency and impregnation processes serve to finish textiles with substances which prevent the deposition of soil or make it easier to wash out. Preferred repellents and impregnating agents are perfluorinated fatty acids, also in the form of their aluminum and zirconium salts, organic silicates, silicones, polyacrylic esters having a perfluorinated alcohol component or polymerizable compounds having a coupled, perfluorinated acyl or sulfonyl radical. Antistats may also be present. The soil-repellent finish with repellents and impregnating agents is often classified as an easycare finish. The penetration of the impregnating agents in the form of solutions or emulsions of the active ingredients in question may be eased by adding wetting agents which lower the surface tension. A further field of use of repellents and impregnating agents is the water-repellent finishing of textiles, tents, tarpaulins, leather, etc., in which, in contrast to waterproofing, the fabric pores are not sealed and the substance thus remains breathable (hydrophobicizing). The hydrophobicizing agents used for the hydrophobicization coat textiles, leather, paper, wood, etc., with a very thin layer of hydrophobic groups such as relatively long alkyl chains or siloxane groups. Suitable hydrophobicizing agents are, for example, paraffins, waxes, metal soaps, etc., with additives of aluminum or zirconium salts, quaternary ammonium compounds having long-chain alkyl radicals, urea derivatives, fatty acid-modified melamine resins, chromium complex salts, silicones, organotin compounds and glutaraldehyde, and also perfluorinated compounds. The hydrophobicized materials do not have a greasy feel, but water drops, similarly to the way they do on greased substances, run off them without wetting them. For example, silicone-impregnated textiles have a soft hand and are water- and soil-repellant. Stains of ink, wine, fruit juices and the like can be removed more easily.

For the care of the textiles and for an improvement in the textile properties such as a softer "hand" (softening) and reduced electrostatic charge (increased wear comfort), the inventive compositions may comprise fabric softeners. The active ingredients in fabric softener formulations are ester quats, quaternary ammonium compounds having two hydrophobic radicals, for example distearyldimethylammonium chloride which, however, owing to its inadequate biodegradability, is increasingly being replaced by quaternary ammonium compounds which contain ester groups in their hydrophobic radicals as intended cleavage sites for biodegradation. Such ester quats having improved biodegradability are obtainable, for example, by esterifying mixtures of methyldiethanolamine and/or triethanolamine with fatty acids and subsequently quaternizing the reaction products with alkylating agents in a manner known per se. Another suitable finish is dimethylolethyleneurea.

To improve the water-absorption capacity, the rewettability of the treated textiles and to ease the ironing of these textiles, it is possible to use silicone derivatives, for example, in the inventive compositions. They additionally improve the rinse-out performance of the inventive compositions by virtue of their foam-inhibiting properties. Preferred silicone derivatives are, for example, polydialkyl- or alkylarylsiloxanes in which the alkyl groups have from 1 to 5 carbon atoms and are fully or partly fluorinated. Preferred silicones are polydimethylsiloxanes which may optionally be derivatized and are in that case amino-functional or quaternized or have Si—OH, Si—H and/or Si—Cl bonds. Further preferred silicones are the polyalkylene oxide-modified polysiloxanes, i.e. polysiloxanes which have polyethylene glycols, for example, and the polyalkylene oxide-modified dimethylpolysiloxanes.

Owing to their fibercare action, protein hydrolyzates are further preferred active substances from the field of detergents in the context of the present invention. Protein hydrolyzates are product mixtures which are obtained by acid-, base- or enzyme-catalyzed degradation of proteins. According to the invention, protein hydrolyzates either of vegetable or animal origin may be used. Animal protein hydrolyzates are, for example, elastin, collagen, keratin, silk and milk protein hydrolyzates which may also be present in the form of salts. Preference is given in accordance with the invention to the use of protein hydrolyzates of vegetable origin, for example soya, almond, rice, pea, potato and wheat protein hydrolyzates. Although preference is given to the use of the protein hydrolyzates as such, it is in some cases also possible to use in their stead amino acid mixtures or individual amino acids obtained in other ways, for example arginine, lysine, histidine or pyroglutamic acid. It is likewise possible to use derivatives of protein hydrolyzates, for example in the form of their fatty acid condensates.

As explained at the outset, spaces are deodorized and fragranced by means of the inventive compositions by introducing these compositions into a space and subsequently heating to temperatures between 30 and 150° C. The present application therefore further provides a method for deodorizing and fragrancing spaces, characterized in that an inventive fragrance release system is introduced into the space and is heated to temperatures between 30 and 150° C. If the inventive fragrance release system is used in an environment where the temperatures are below the melting or softening temperature for the material of the particles used, it has to be activated by carrying out a heat treatment before use. Possible use locations are therefore: restrooms, passenger cells, toilet bowls, trash cans, closets.

Suitable for fragrancing are generally all closed spaces, but in particular the interiors of buildings, vehicles or appliances, preferably such as textile washing machines, dryers or machine dishwashers.

The use of inventive fragrance release systems for deodorizing and fragrancing closed or open spaces is further provided by the present application.

As used herein, and in particular as used herein to define the elements of the claims that follow, the articles "a" and "an" are synonymous and used interchangeably with "at least one" or "one or more," disclosing or encompassing both the singular and the plural, unless specifically defined otherwise. The conjunction "or" is used herein in its inclusive disjunctive sense, such that phrases formed by terms conjoined by "or" disclose or encompass each term alone as well as any combination of terms so conjoined, unless specifically defined otherwise. All numerical quantities are understood to be modified by the word "about," unless specifically modified otherwise or unless an exact amount is needed to define the invention over the prior art.

What is claimed is:

1. A fragrance release system comprising a substantially rotationally symmetric container having a chamber accommodating a multitude of particles for deodorizing or fragrancing an open or closed space, said particles comprising a carrier material and at least one fragrance, and said container having a plurality of orifices through which emission of the fragrances of the particles from the accommodation chamber outward is possible, wherein the accommodation chamber (3) of the substantially rotationally symmetric container (2) has a crescent-like cross-sectional shape with a convex front wall (5) and a concave back wall portion (6), wherein the accommodation chamber (3) is filled virtually fully with particles (4) and wherein the container (2) is in two parts, one part (2') having the wall (6) and the other part (2") having the front part wall (5).

2. The fragrance release system of claim 1, wherein the two and end regions(7) of the crescent-like cross sectional shape of the accommodation chamber (3) are rounded.

3. The fragrance release system of claim 1, wherein the part (2') having the back wall (6) of the container (2) has a bulge-like edge region (8) which is connected to a strut- like edge region (9) of the other part(2").

4. The fragrance release system of claim 3, wherein the two parts (2', 2") are connected to one another by means of a snap-in connection (9, 10).

5. The fragrance release system of claim 1, wherein the concave back wall (6) curves inward in a conelike manner in the middle region thereof (15).

6. The fragrance release system of claims 1, having a ratio of the total surface area of all particles (4) in the starting state to the total surface area of the accommodation chamber (3) of 1:0.35 to 1:0.36.

7. The fragrance release system of claim 1, wherein the particles (4) in the accommodation chamber (3) filled nearly fully with particles (4) have a layer thickness of is between 10 and 12 mm.

8. The fragrance release system of claim 1, wherein the the accommodation chamber (3) has a volume of 10 to 500 ml.

9. The fragrance release system of claim 8, wherein the the accommodation chamber (3) has a volume 40 ml.

10. The fragrance release system of claim 1, wherein the container (2) has on its exterior a securing means.

11. The fragrance release system of claim 1, wherein a multitude of slot-shaped orifices (13, 14) is provided in the region of the back wall (6).

12. The fragrance release system of claim 1, wherein the carrier material comprises a polymeric material and has a melting or softening point of 30 to 150° C.

13. The fragrance release system of claim 12, wherein the carrier material has a melting or softening point of 40 to 125° C.

14. The fragrance release system of claim 13, wherein the carrier material has a melting or softening point of 60 to 100° C.

15. The fragrance release system of claim 14, wherein the carrier material has a melting or softening point of 70 to 90° C.

16. The fragrance release system of claim 15, wherein the carrier material has a melting or softening point of 75 to 80° C.

17. The fragrance release system of claim 1, wherein the carrier material comprises at least one substance selected from the group consisting of ethylene/vinyl acetate copolymers, low- or high-density polyethylene (LDPE, HDPE) or mixtures thereof, polypropylene, polyethylene/polypropylene copolymers, polyether/polyamide block copolymers, styrene/butadiene (block) copolymers, styrene/isoprene (block) copolymers, styrene/ethylene/butylene copolymers, acrylonitrile/butadiene/styrene copolymers, acrylonitrile/butadiene copolymers, polyether esters, polyisobutene, polyisoprene, ethylene/ethyl acrylate copolymers, polyamides, polycarbonate, polyester, polyacrylonitrile, polymethyl methacrylate, polyurethanes, polyvinyl alcohols, and any combinations or mixtures thereof.

18. The fragrance release system of claim 17, wherein the carrier material comprises at least 10% by weight ethylene/vinyl acetate copolymer.

19. The fragrance release system of claim 18, wherein the carrier material comprises at least 30% by weight ethylene/vinyl acetate copolymer.

20. The fragrance release system of claim 19, wherein the carrier material comprises at least 70% by weight ethylene/vinyl acetate copolymer.

21. The fragrance release system of claim 20, wherein the carrier material consists of ethylene/vinyl acetate copolymer.

22. The fragrance release system of claim 1, wherein the carrier material comprises an ethylene/vinyl acetate copolymer that comprises 5 to 50% by weight of vinyl acetate.

23. The fragrance release system of claim 22, wherein the carrier material comprises an ethylene/vinyl acetate copolymer that comprises 10 to 40% by weight of vinyl acetate.

24. The fragrance release system of claim 23, wherein the carrier material comprises an ethylene/vinyl acetate copolymer that comprises 20 to 30% by weight of vinyl acetate.

25. The fragrance release system of claim 1, wherein the particles comprise 1 to 70% by weight of one or more fragrances.

26. The fragrance release system of claim 25, wherein the particles comprise 10 to 60% by weight of one or more fragrances.

27. The fragrance release system of claim 26, wherein the particles comprise 20 to 50% by weight of one or more fragrances.

28. The fragrance release system of claim 27, wherein the particles comprise 30 to 40% by weight of one or more fragrances.

29. The fragrance release system of claim 1, wherein the particles (4) have an average diameter of 0.5 to 20 mm.

30. The fragrance release system of claim 29, wherein the particles (4) have an average diameter of 0.1 to 10 mm.

31. The fragrance release system of claim 30, wherein the particles (4) have an average diameter of 0.3 to 6 mm.

32. The fragrance release system of claim 1, comprising one or more further active substances selected from the group of the perfume carriers, dyes, active antimicrobial ingredients, germicides, fungicides, antioxidants or corrosion inhibitors.

33. The fragrance release system of claim 1, wherein the container (2) comprises one or more water-insoluble organic or inorganic materials.

34. The fragrance release system of claim 1, wherein the particles (4) have been heat-treated within the temperature range of the melting or softening point of the carrier material.

35. The fragrance release system of claim 34, wherein the particles (4) have been heat-treated within the temperature range of the carrier material melting or softening point before or in the course of use of the fragrance release system.

36. A method for deodorizing and fragrancing a space, comprising the steps of introducing into the space a fragrance release system comprising a substantially rotationally symmetric container having a chamber accommodating a multitude of particles for deodorizing or fragrancing an open or closed space, said particles comprising a carrier material and at least one fragrance, and said container having a plurality of orifices through which emission of the fragrances of the particles from the accommodation chamber outward is possible, wherein the accommodation chamber (3) of the substantially rotationally symmetric container (2) has a crescent-like cross-sectional shape with a convex front wall (5) and a concave back wall portion (6), and heating the system to a temperature between 30 and 150° C. before or during use.

37. The method of claim 36, wherein the space comprises an interior of a building, vehicle, or appliance.

38. The method of claim 36, wherein the space comprises an interior of a toilet, passenger cell, closet, trash can, machine dishwasher, washing machine, or dryer.

* * * * *